(12) United States Patent
Oku et al.

(10) Patent No.: US 6,448,001 B2
(45) Date of Patent: Sep. 10, 2002

(54) ANALYTICAL METHOD, KIT, AND APPARATUS

(75) Inventors: Yuichi Oku; Yoshitatsu Tanaka; Yoko Otsuka, all of Ibaraki (JP)

(73) Assignee: Nissui Pharmaceutical Co., Ltd. (JP)

( * ) Notice: Subject to any disclaimer, the term of this patent is extended or adjusted under 35 U.S.C. 154(b) by 0 days.

(21) Appl. No.: 09/171,617

(22) PCT Filed: Mar. 2, 1998

(86) PCT No.: PCT/JP98/00857

§ 371 (c)(1),
(2), (4) Date: Oct. 22, 1998

(87) PCT Pub. No.: WO98/40740

PCT Pub. Date: Sep. 17, 1998

(30) Foreign Application Priority Data

Mar. 10, 1997 (JP) ............................................. 9-72649

(51) Int. Cl.$^7$ .............................. C12Q 1/68; C12Q 1/70
(52) U.S. Cl. ............................... 435/6; 435/5; 435/7.1; 436/501; 436/514; 436/518
(58) Field of Search .................. 435/6, 5, 7.1; 436/501, 436/514, 518

(56) References Cited

U.S. PATENT DOCUMENTS

| | | | |
|---|---|---|---|
| 4,861,711 A | * | 8/1989 | Friesen et al. ................. 436/7 |
| 4,868,105 A | * | 9/1989 | Urdea et al. .................... 435/6 |
| 4,921,788 A | * | 5/1990 | Deutsch .......................... 435/6 |
| 5,569,582 A | * | 10/1996 | Tavernarakis et al. ......... 435/5 |
| 5,591,645 A | * | 1/1997 | Rosenstein ................... 436/514 |
| 5,795,714 A | * | 8/1998 | Cantor et al. .................. 435/6 |

FOREIGN PATENT DOCUMENTS

| | | |
|---|---|---|
| JP | 6-186232 | 7/1994 |
| JP | 8-94618 | 4/1996 |
| WO | 94/27150 | 11/1994 |

* cited by examiner

Primary Examiner—Jeffrey Fredman
Assistant Examiner—Juliet Einsmann
(74) Attorney, Agent, or Firm—Lorusso & Loud

(57) ABSTRACT

Providing an assay method capable of simultaneously determining the presence or absence of one or more species of biological substances or assaying the amounts thereof with a single assay device, a kit therefor and an assay device thereof. The amount thereof or the presence thereof is detected, by putting a liquid sample containing one or more species of analytes in contact to a reagent including one or more species of marker-labeled ligands and one or more species of nucleic acid-labeled ligands, to generate one or more species of complexes, developing the generated one or more species of complexes through capillary phenomenon in developing element 11 in a sheet form, capturing the complexes through complementary nucleic acid binding onto anti-bond elements consisting of nucleic acids on detection zones 15, 16 and 17 formed depending on each of one or more species of nucleic acids immobilized on the detection zone 14, thereby capturing a complex depending on the analyte species, through the complementary binding between the anti-bond element and the bond element, to form an independent band and to assay the amount or the presence on the detection part.

24 Claims, 8 Drawing Sheets

Assay reagent of one or more species of antigens, the reagent is capable of simultaneously assaying antigens A, B and C αA, αB and αC: respective antibodies against antigens A, B and C ON1: oligonucleotide with a sequence different from those of ON2 and ON3

ON2: oligonucleotide with a sequence different from those of ON1 and ON3

ON3: oligonucleotide with a sequence different from those of ON1 and ON2

M: marker

Fig.1

Assay reagent of one or more species of antigens, the reagent is capable of simultaneously assaying antigens A, B and C

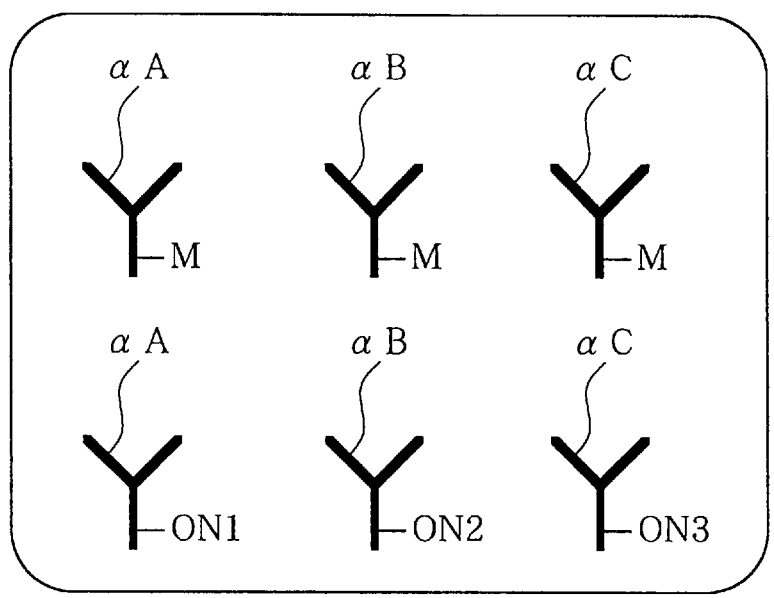

αA, αB and αC: respective antibodies against antigens A, B and C

ON1: oligonucleotide with a sequence different from those of ON2 and ON3

ON2: oligonucleotide with a sequence different from those of ON1 and ON3

ON3: oligonucleotide with a sequence different from those of ON1 and ON2

M: marker

ON1': oligonucleotide with a complementary nucleotide sequence to ON1

ON2': oligonucleotide with a complementary nucleotide sequence to ON2

ON3': oligonucleotide with a complementary nucleotide sequence to ON3

Ⓐ : Antigen A

🄱 : Antigen B

△C : Antigen C

αA, αB : the same as in Fig. 1
ON1, ON2, ON3 : the same as in Fig. 1
M : the same as in Fig. 1
Ⓒ : antigen C

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: biotinylated oligonucleotide

<400> SEQUENCE: 1

```
gaattcccgg ggatccgtcg                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      biotinylated oligonucleotide

<400> SEQUENCE: 2
cgacggatcc ccgggaattt c                                                  21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      biotinylated oligonucleotide

<400> SEQUENCE: 3
aacggaatct aatcaggagg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      biotinylated oligonucleotide

<400> SEQUENCE: 4
cctcctgatt agattccgtt                                                    20
```

ANALYTICAL METHOD, KIT, AND APPARATUS

TECHNICAL FIELD

The present invention relates to an assay method for assaying an analyte as a biological assay subject or for detecting the presence or absence thereof, which is useful for simple clinical diagnosis, and a kit and an assay device to be used for the method; more specifically, the present invention relates to an assay method for assaying a great number of combinations of one or more species of analytes contained in a fluid sample or the presence or absence thereof, and a kit and an assay device therefor.

BACKGROUND ART

For determining the disease affecting a patient in a laboratory test, several types of laboratory test results should collectively be examined. In general, patients should undergo several types of such tests for appropriate diagnosis and therapeutic treatment. However, one laboratory reagent can assay or detect one item in most cases in the prior art, so the sample volume drawn from a patient is increased in proportion to the number of tests, which works a physical burden on the patient.

Alternatively, it is required to carry out conventional immunological tests by using automatic assay devices, so the sample drawn from a patient is delivered to an institute equipped with such automatic assay devices, where the tests are conducted, and then, the test results are reported to the doctor. In such manner, the doctor can make diagnosis based on the results and the clinical conditions of the patient. Therefore, such device works as one cause of delay treatment because the doctor cannot make a decision instantly.

So as to overcome such problem, a method comprising a combination of immune reaction and chromatography (abbreviated as "immunochromatography" herein below) has been developed in recent years. The standard principle of conventional immunochromatography will now be described below.

In the assay device to be used for the conventional immunochromatography, the following zones are arranged; a loading zone for loading a fluid sample containing an analyte, at one end of a developing element in the form of porous sheet such as nitrocellulose film, a water absorption zone for receiving the fluid transferred through capillary action in the developing element, at the other end, a sealing zone containing a marker-labeled immune substance, located on a side close to the loading zone between the water absorption zone and the loading zone, and a detection zone where an immune substance to bind a complex composed of the analyte and the labeled substance is immobilized, the zone being arranged on a side apart from the loading zone.

By the assay method by using such assay device, a fluid sample containing an analyte to be assayed is firstly loaded on the loading zone, and the fluid sample is then transferred through capillary action to the sealing zone containing a marker-labeled immune substance. In the sealing zone, the marker-labeled immune substance and the analyte are bound together through immunological affinity, to form a marker-labeled immunocomplex. The marker-labeled immunocomplex is developed and transferred, through capillary action and/or diffusion in the developing element, to the detection zone, where an immune substance immobilized in the detection zone captures the complex. The marker in the marker-labeled immunocomplex captured in the detection zone is assayed or detected, whereby the amount or presence of the analyte contained in the fluid sample can be assayed.

Compared with enzyme immunoassay, another assay for immunochemical active substances, the method is characteristic in that no rinsing procedure is required during an intermediate stage of assaying and the assay can be done under naked eyes, essentially never requiring any device to detect the marker, and in that the reagent contained in the assay device is kept at dry state so it can be stored at ambient temperature for a long term. According to the conventional immunochromatography, a doctor can instantly examine a sample collected by himself, and hence, the doctor can inclusively take into account clinical conditions of a patient and the immunological test results of the patient, to diagnose the patient in a short time. Accordingly, the delay in the treatment will be less, advantageously.

A number of patent application have been laid open concerning immunochromatography. For example, the immunochromatography described in Japanese Patent Publication No. Hei 7-13640 is essentially the same as the prior art immunochromatography described above, characterized in that a ligand bound to an insoluble vesicle marker is used and the insoluble vesicle marker is colored liposome, colored polymer bead, or metal or polymer dye particle. However, the publication does not include any description about the simultaneous assay or detection of one or more species of biological substances such as antigen or antibody.

Japanese Patent No. 2504923 describes an immunochromatography essentially the same as the prior art immunochromatography, suggesting an analysis by a sandwich method wherein a complex captured in a detection zone is a marker-labeled receptor-analyte-receptor as well as simultaneous detection of a first analyte and a second analyte, having biological affinities different from each other. However, the publication does not suggest that the marker-labeled immunocomplex is captured through the complementary binding between the bases of nucleic acids in a detection zone or the applicability of the method to two or more analytes or the assay sensitivity thereof.

Alternatively, immunoassay methods can yield higher sensitivity when a large amount of immunochemically active substances can be immobilized, and in that case, the methods can detect the same levels of immunochemically active substances in a shorter time. Hence, a more highly sensitive assay technique in the field of immunochromatography has been desired.

It is thus an object of the present invention to provide an assay method useful for clinical diagnosis, which can simultaneously assay one or more species of biological substances or detect the presence or absence thereof, at a higher sensitivity, by means of a single assay device in a simple fashion, and a kit and an assay device for the assay.

DISCLOSURE OF INVENTION

A first aspect of the assay method of the present invention is an assay method by means of a kit, wherein a reagent and an assay device are separately arranged. The assay method is an assay method for assaying the amounts of one or more species of analytes present in a fluid sample or detecting the presence or absence thereof, comprising:

(1) putting a fluid sample containing one or more species of analytes in contact to a reagent containing one or more species of marker-labeled ligands each produced by binding a marker to a first ligand, and one or more species of bond element-labeled ligands each produced by binding a bond element consisting of nucleic acids with a predetermined base sequence depending on the analyte species, to a second ligand, to generate one or more species of specific complexes each composed of a specific analyte species, a specific marker-labeled ligand species specifically binding to the specific analyte species, and a specific bond element-labeled ligand species specifically binding to the specific analyte species;

(2) developing one or more species of generated complexes through capillary action in a developing element in a sheet form;

(3) capturing a complex depending on the analyte species, through the complementary binding between the bond element and an anti-bond element, in the detection zone produced by immobilizing independently anti-bond elements consisting of nucleic acids each having a complementary sequence to the base sequence of one bond element species in the complexes, thereby forming an independent band; and (4) assaying or detecting the marker formed in the band in the detection zone.

Another embodiment of the assay method of the present invention is a method using an assay device integrally containing a reagent. The assay method is an assay method for assaying the amounts of one or more species of analytes present in a fluid sample or detecting the presence or absence thereof, comprising:

(1) loading a fluid sample containing one or more species of analytes on a developing element in a sheet form, thereby developing the fluid sample through capillary action in the developing element;

(2) transferring the fluid sample to put the sample in contact to a sealing zone sealing therein reagent components including one or more species of marker-labeled ligands each produced by binding a marker to a first ligand specifically reactive to a specific analyte species, and one or more species of bond element-labeled ligands each produced by binding a bond element consisting of nucleic acids with a predetermined base sequence depending on the analyte species, to a second ligand specifically reactive to the specific analyte species;

(3) developing one or more species of specific complexes each composed of a specific analyte species, a specific marker-labeled ligand species specifically binding to the specific analyte species, and a specific bond element-labeled ligand species specifically binding to the specific analyte species, or developing a reaction product under way of formation, through capillary action in the developing element;

(4) capturing complex depending on the analyte species through complementary binding between the bond element and an anti-bond element and forming an independent band therefor in a detection zone where each anti-bond element species having the complementary base sequence to the sequence of one bond element species in the complex is immobilized; and (5) assaying or detecting the marker contained in the band formed in the detection zone.

The assay kit of the present invention is an assay kit for assaying one or more species of analytes in a sample or detecting the presence or absence thereof in a sample, the assay kit comprising a reagent and an assay device of a separate type from the reagent, wherein the reagent includes one or more species of marker-labeled ligands each produced by binding a marker to a first ligand specifically reactive to a specific analyte species, and one or more species of bond element-labeled ligands each produced by binding a bond element consisting of nucleic acids with a predetermined base sequence depending on the specific analyte species, to a second ligand specifically reactive to the specific analyte species; and wherein the assay device includes a developing element in a sheet form, the developing element can develop analytes, reagent and analytes bound to the reagent through capillary action, and one or more species of anti-bond elements comprising a nucleic acid with a base sequence complementary to a bond element contained in the separate reagent are independently each kind immobilized in the detection zone of the developing element, whereby a complex of each analyte species is captured through the complementary binding between the bond element and an anti-bond element in the detection zone, thereby forming an independent band.

The assay device of the present invention characteristically is an assay device contained in the assay kit.

Furthermore, the assay device of the present invention is an assay device for assaying one or more species of analytes present in a sample or detecting the presence or absence thereof in the sample, wherein the assay device includes, (1) a developing element in a sheet form, being capable of developing analytes, reagent and analytes bound to the reagent;

(2) a loading zone to receive a fluid sample from outside, the loading zone being positioned at one end of the developing element in a sheet form and capable of receiving a fluid sample from outside and having a sufficient feeding potency to transfer the received fluid sample to the other end to supply the fluid sample to be analyzed to a sealing zone sealing therein the reagent components;

(3) a sealing zone sealing therein reagent components including one or more species of marker-labeled ligands each produced by binding a marker to a first ligand specifically reactive to a specific analyte species, and one or more species of bond element-labeled ligands each produced by binding a bond element consisting of nucleic acids with a predetermined base sequence depending on the analyte species, to a second ligand specifically reactive to the specific analyte species, the sealing zone being arranged at a position close to the loading zone;

(4) a water absorption zone arranged at a position apart from the loading zone, the zone being capable of receiving the analytes, reagent and analytes bound to the reagent, after diffusion in the developing element; and (5) a detection zone positioned between the sealing zone and the water absorption zone, where one or more species of anti-bond elements each with a base sequence complementary to one bond element are immobilized, whereby a complex formed from a marker-labeled ligand, an analyte species and a bond element-labeled ligand, depending on the analyte species, can be captured and detected.

In accordance with the present invention, one or more species of analytes can be assayed with a single kit or assay device at a high sensitivity.

In accordance with the present invention, the term "ligand" means a molecule having a biological affinity with an analyte and being capable of specifically reacting with a specific analyte species, to form a pair. In accordance with the present invention, the term "first ligand" and "second ligand" may have the same properties or may not have the same properties. If an analyte is an antigen, the first ligand and the second ligand may be antibodies; if an analyte is an antibody, the first ligand and the second ligand may be antigens. Another example of the combination of the analyte and ligands includes a combination of a receptor and ligands capable of binding to the receptor, a combination of a nucleic acid and complementary nucleic acids capable of binding to nucleic acids, a combination of lectin and specific sugars capable of binding to lectin.

In accordance with the present invention, the term "bond element" means a nucleic acid which does not bind to an analyte but has a reactivity different from those ligands. In accordance with the present invention, the term "anti-bond element" means a nucleic acid with a base sequence at least partially complementary to the base sequence of the "bond element", and the anti-bond element binds to the bond element in a complementary fashion. The combination of the "bond element" and the "anti-bond element" includes nearly infinite numbers of combinations, depending on the base sequences of nucleic acid molecules composing the bond element and the anti-bond element. From the respect of the complementary binding between the bond element and the anti-bond element, individual base sequences may satisfactorily be partially complementary or completely complementary to each other. As the nucleic acids functioning as the bond element and anti-bond element, use may be made of DNA, RNA, oligonucleotide, and polynucleotide, preferably including an oligonucleotide of a length of 10 mer or more to 100 mer or less.

Directly or indirectly through a substance, the anti-bond elements are bound and immobilized on the developing element in a detection zone. For example, the anti-bond elements are directly immobilized on the developing element, by covalently bonding a nucleic acid as the anti-bond element, through a functional group introduced into 5' or 3' terminus of a nucleic acid or introduced into a base of a nucleic acid, to a functional group contained in an insoluble support as the developing element. Depending on the one or more species of analytes to be assayed, individually different base sequences are predetermined for the anti-bond elements and are immobilized separately from each other, in the form of zones in the detection zone.

Through biotin introduced into 5' or 3' terminus of a nucleic acid or through biotin introduced into a nucleotide composing a nucleic acid, nucleic acids as anti-bond elements are bound to avidins or streptoavidins preliminarily bound to an insoluble support as the developing element, whereby nucleic acids can be immobilized on the developing element indirectly. By binding a nucleic acid, through a functional group introduced into 5' or 3' terminus of nucleic acid or introduced into a base of the nucleic acid, to a protein and then binding the nucleic acid-bound protein to an insoluble support as the developing element, nucleic acids as an anti-bond element can indirectly be immobilized on the developing element.

As a reagent component to be used in accordance with the present invention, use may be made of "marker-labeled ligand" produced by binding a marker to a first ligand, and "bond element-labeled ligand" produced by binding a bond element consisting of nucleic acids with a predetermined base sequence, depending on the analyte species, to a second ligand. Separately from the developing element, the reagent component can compose a kit to be used in combination with the developing element. Additionally, the reagent component may satisfactorily be retained at a dry state in the sealing zone of the developing element.

As a marker contained in the marker-labeled ligand, specifically, use may be made of enzymatically active molecules, digoxigenin, metal colloid, colored latex, colored liposome, nucleic acid, biotin, avidin, fluorescent substance, luminescent substance, radioisotope and the like. Herein, the meaning of the term "coloring" is not limited to the deposition of a color which can be discriminated visually, but includes the deposition of fluorescent substances and luminescent substances.

In accordance with the present invention, the "developing element" is in the form of sheet, and can develop analytes, reagent and analytes bound to the reagent in a chromatographic fashion. Preferably as the developing element, use may be made of porous insoluble supports, more specifically including plastic porous supports, cellulose porous supports and inorganic porous supports; still more specifically, use may be made of cellulose, nitrocellulose, cellulose acetate, nylon, silica or derivatives thereof, all being porous. In the individual multiple zones formed on the developing element, different materials may be used or used in combination. In some case, one face of each of plural zones may be reinforced with the same material as the material on the other face or with a different material from the material on the other face. Additionally, these zones may generally be dry if not used for assay.

BRIEF DESCRIPTION OF DRAWINGS

FIG. 1 schematically depicts one example of the reagent as one component of the assay kit for one or more species of subjective analytes in accordance with the present invention;

BEST MODE OF CARRYING OUT THE INVENTION

FIG. 1 schematically depicts one example of the reagent as one component of the assay kit for one or more species of analytes in accordance with the present invention, wherein the analytes are three species of antigens, namely antigens A, B and C. In FIG. 1, all components in the frame are contained in one reagent, and the reagent may be present in dry state or present in a liquid. In FIG. 1, $\alpha A$, $\alpha B$ and $\alpha C$ represents individual antibodies against antigens A, B and C, respectively. The antibodies $\alpha A$, $\alpha B$ and $\alpha C$ are bound with individual markers, so these antibodies serve as marker-labeled antibodies. The markers introduced into the individual antibodies may be the same or different. Three species of antibodies, namely $\alpha A$, $\alpha B$ and $\alpha C$, bound with oligonucleotides ON1, ON2 and ON3, having different sequences from each other, are contained in the reagent, and these three are defined as antibodies-oligonucleotides-bound products. The reagent composing the assay kit may be in a liquid or dry state.

Figure 2:
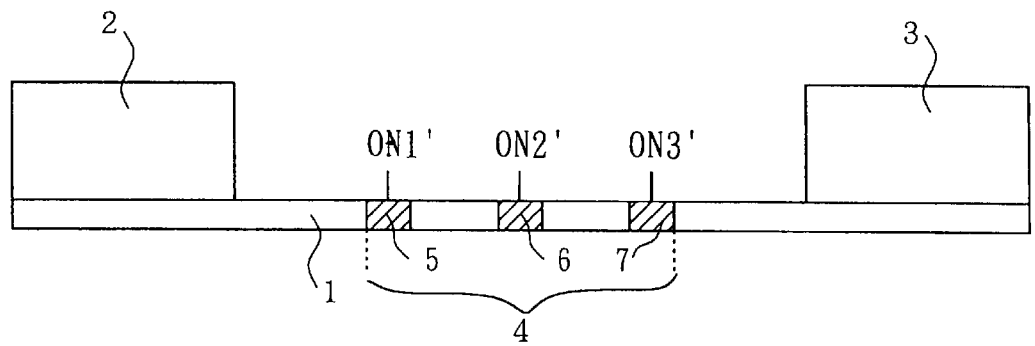
FIG. 2 schematically depicts one example of the assay device as one component of the assay kit in accordance with the present invention.

FIG. 2 schematically depicts one example of the assay device as one component of the assay kit in accordance with the present invention, which may be used in combination with the reagent of FIG. 1. In FIG. 2, 1 represents a developing element comprising a strip piece of porous sheet; 2 represents a loading zone arranged at one end of the developing element 1 to absorb a loaded liquid sample and a reagent mixture to supply them to the developing element 1; 3 represents an absorption zone capable of receiving analytes, reagent and analytes bound to the reagent, after transferred and diffused along the developing element. Between the loading zone 2 and the absorption zone 3 is arranged detection zone 4. Detection zone 4 includes first detection zone 5 with immobilized oligonucleotide ON1' with a complementary base sequence to oligonucleotide ON1, second detection zone 6 with immobilized oligonucleotide ON2' with a complementary sequence to oligonucleotide ON2 and third detection zone 7 with immobilized oligonucleotide ON3' with a complementary sequence to oligonucleotide ON3' with zones 5, 6 and 7 individually formed separately in a stripe pattern.

A simple clinical diagnostic method by using the assay kit comprising a combination of the reagent of FIG. 1 and the developing element of FIG. 2 will now be explained. By using a liquid sample containing antigens A, B and C as analytes, the sample is mixed with the reagent in a container, for effecting an immunological affinity reaction. The resulting reaction solution is loaded on the loading zone 2 of the developing element 1. The reaction solution may satisfactorily be loaded in such a manner that the loading zone 2 is immersed with the reaction solution or the reaction solution is dropwise added into the loading zone 2 or the reaction solution is coated on the zone 2. The reaction solution contains analytes, reagent and marker-labeled immunocomplexes of the analytes complexed with the reagent. The reaction solution is transferred or diffused by capillary action through the developing element 1 to the detection zone 4, where the marker-labeled immunocomplexes are captured through the complementary binding between an immobilized oligonucleotide with a base sequence preliminarily determined on the basis of each analyte species, and an oligonucleotide contained in the marker-labeled immunocomplexes.

Figure 3:
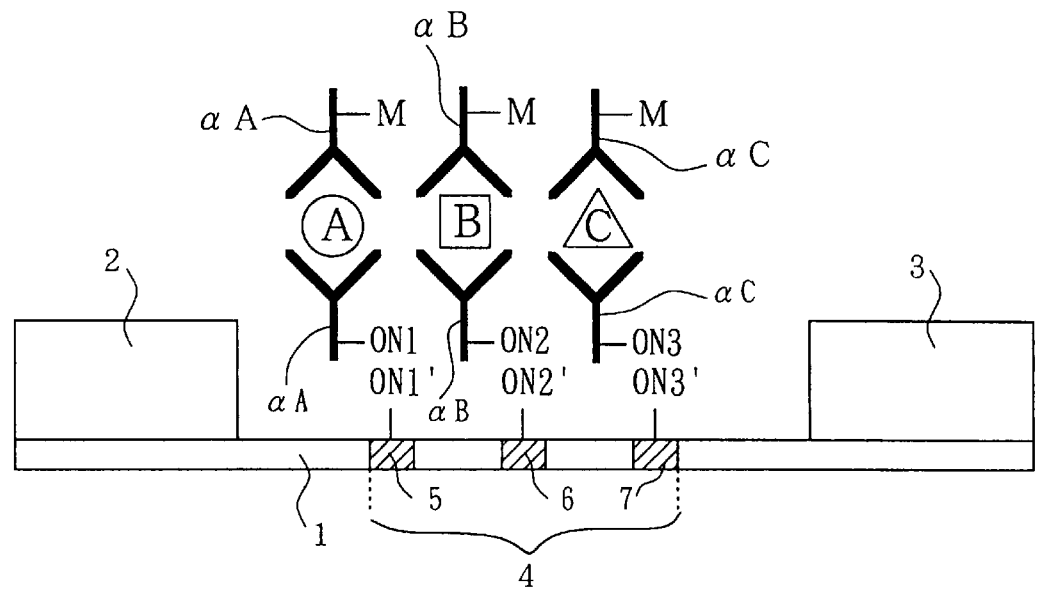
FIG. 3 schematically depicts the state of the marker-labeled immunocomplexes captured, depending on the analyte species, by a simple clinical diagnostic method using the assay kit shown in FIGS. 1 and 2.

FIG. 3 schematically depicts the state of the marker-labeled immunocomplexes captured, depending on the analyte species, by a simple clinical diagnostic method using the assay kit shown in FIGS. 1 and 2.

As the reagent components of the present invention, the first ligand contained in the marker-labeled ligand and the second ligand contained in a nucleic acid-labeled ligand may have the same reactivity or a different reactivity from each other. Additionally, the combination of the first ligand with the second ligand may be a combination of a monoclonal antibody and a polyclonal antibody, both against the same antigen, a combination of polyclonal antibodies, and a combination of monoclonal antibodies with different binding sites.

In accordance with the present invention, a mixture of analytes contained in a liquid sample as assay subjects can be assayed, the analytes being independent compounds never belonging to the same category. For example, antigen, antibody and nucleic acid may simultaneously be assayed. In accordance with the present invention, additionally, antagonistic or non-antagonistic assay methods of a variety of patterns may be applicable, with no specific limitation to the sandwich mode as described above.

Because a nearly infinite number of base sequences may be available as the base sequence composing nucleic acid, an infinite number of analytes are detectable in the detection zone.

Figure 4:
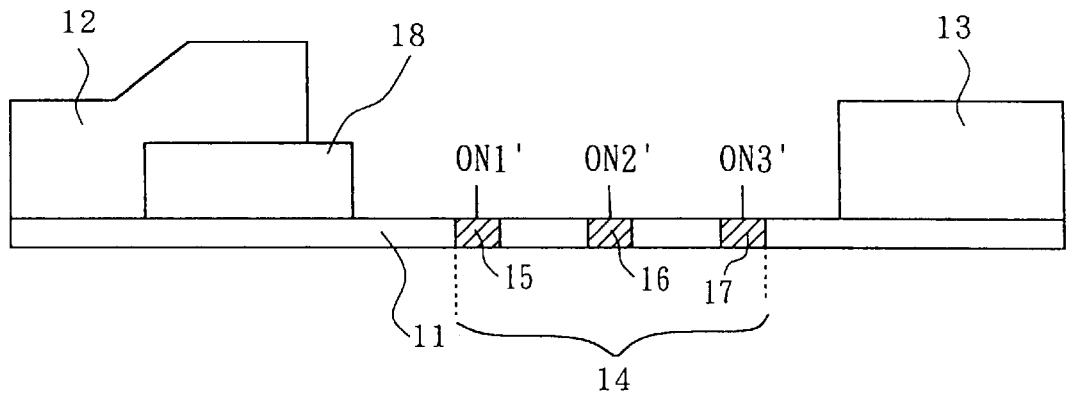
FIG. 4 depicts another embodiment of the assay device of the present invention, which is an assay device integrally including reagent(s) in a dry state.

FIG. 4 depicts another embodiment of the assay device of the present invention, which is an assay device integrally a including a dry reagent. In the assay device of FIG. 4, 11 represents a developing element principally comprising a strip of a band-like porous sheet which is bonded to a reinforcing sheet if needed: 12 represents a loading zone arranged at one end of the developing element 11, to absorb a loaded liquid sample, to feed the liquid sample to the sealing zone 18 and the developing element 11 containing the reagent; 13 represents an absorption zone capable of receiving analytes, the reagent and analytes bound with the reagent, after transferred and diffused through the developing element 11. The difference from the assay device shown in FIG. 2 is that the sealing zone 18 sealing therein reagent components is arranged in close contact between the developing element 11 and the loading zone 12, so that the liquid sample fed from the loading zone 12 to the sealing zone 18 might be transferred to the developing element 11.

Detection zone 14 is arranged in the developing element 11 between the sealing zone 18 and the absorption zone 13, wherein first detection zone 15 with immobilized oligonucleotide ON1' with a complementary base sequence to oligonucleotide ON1, second detection zone 16 with immobilized oligonucleotide ON2' with a complementary sequence to oligonucleotide ON2 and third detection zone 17 with immobilized oligonucleotide ON3' with a complementary sequence to oligonucleotide ON3 are individually formed separately in a stripe pattern.

Figure 5:
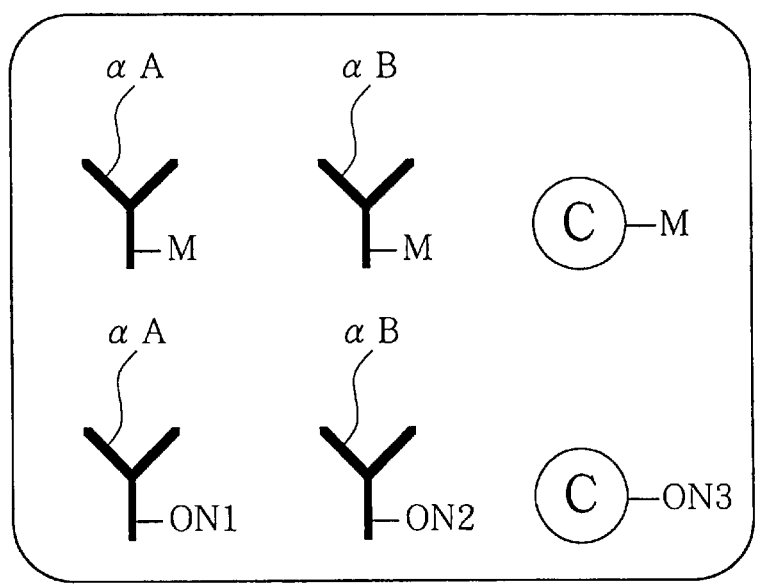
FIG. 5 depicts one example as to how to use the assay device of FIG. 4, wherein the composition of the reagent contained in a dry state in sealing zone 18 of the assay device is shown provided that the subjective analytes are antigens A, B and C.

As an example as to how to use the assay device of FIG. 4, a case is described wherein a liquid sample to be assayed actually contains only antigen A and antibody C, provided that the subject analytes are antigens A and B and antibody C. FIG. 5 depicts the composition of the reagent contained in a dry state in the sealing zone 18 in this case. Compared with the reagent composition of FIG. 1, the reagent composition of the present embodiment is simply modified as follows; the marker-labeled antibody αC is replaced by marker-labeled antigen C; and oligonucleotide ON3-labeled antibody αC is replaced by oligonucleotide ON3-labeled antigen C.

Figure 6:
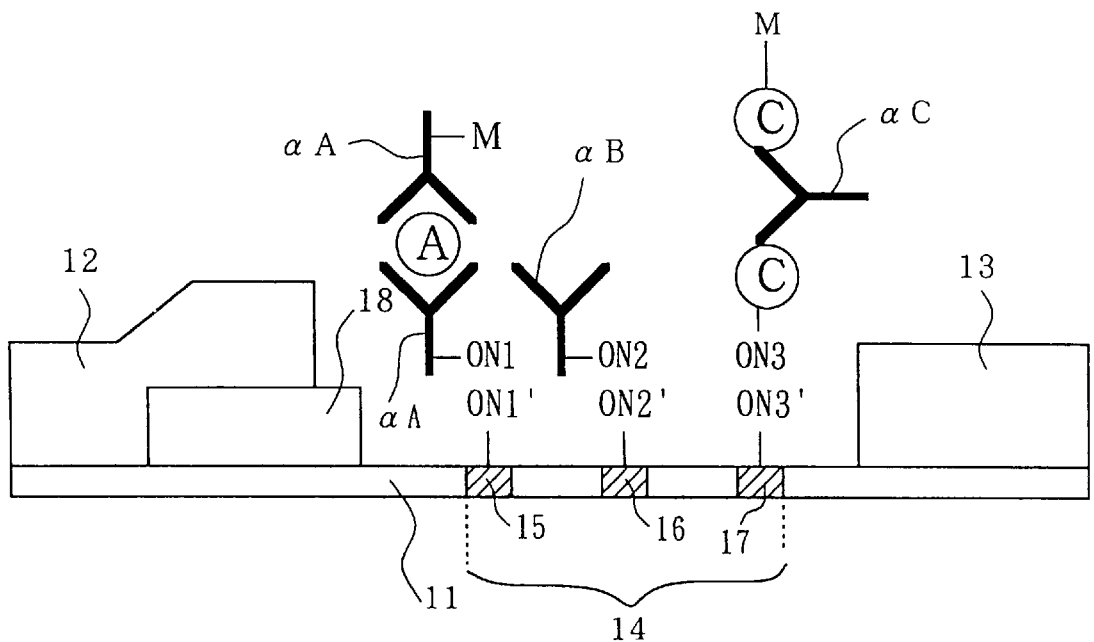
FIG. 6 schematically depicts the state of the marker-labeled immunocomplexes captured, depending on the analyte species, by a simple clinical diagnostic method using the assay device shown in FIG. 4.
Figure 7:
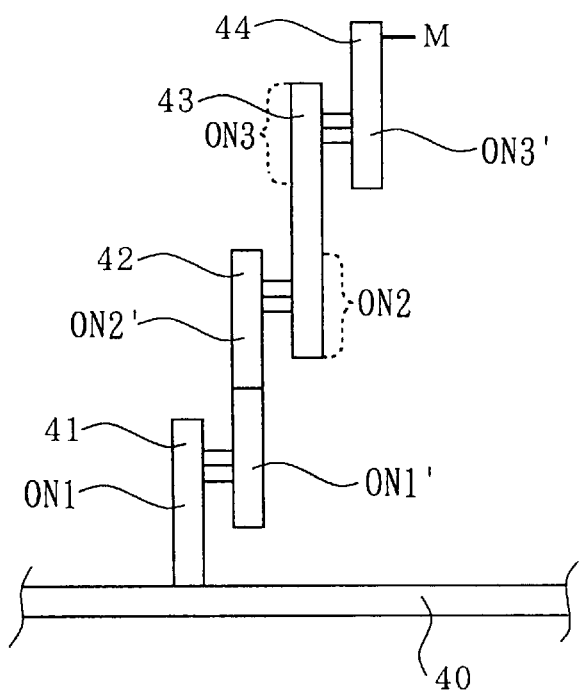
FIG. 7 depicts the principle as to how to capture a nucleic acid as the analyte in the detection zone according to the present invention, wherein the analyte is the nucleic acid containing the oligonucleotides ON3 and ON2 in the sequence thereof.

When a liquid sample containing the analytes antigens A and C is loaded on the loading zone 12, the antigen A forms a sandwich immunocomplex with the marker-labeled antibody αA and oligonucleotide ON1-labeled antibody αA, while the analytes are transferred together with the reagent component through capillary action to the first detection zone 15 for antigen A assay, where the antigen A is captured through the base sequences of oligonucleotides complementary to each other. The antibody C forms a sandwich immunocomplex with the marker-labeled antigen C and oligonucleotide ON3-labeled antigen C, and, upon reaching the third detection zone 17, the antibody C is captured through the complementary base sequences of oligonucleotides to each other. Because antigen B is not present in the liquid sample, no sandwich immunocomplex is formed, and therefore, oligonucleotide ON2-labeled antibody αB is captured, in the second detection zone 16 for antigen B assay. The antigens A and C are assayed or the presence thereof is detected in the markers contained in the sandwich immunocomplexes thus captured on the individual detection zones 15, 16 and 17, so that the absence of antigen B is indicated. FIG. 6 schematically depicts the appearance of the marker-labeled immunocomplexes each captured depending on each species of analytes. FIG. 7 depicts the principle as to how to capture nucleic acids in the detection zones in accordance with the present invention. In FIG. 7, the analyte 43 is a nucleic acid containing oligonucleotides ON3 and ON2 in the sequence. The principle may satisfactorily be applicable to the analyte which is a single-stranded nucleic acid or a double-stranded nucleic acid. The anti-bond element 41 immobilized in the detection zone 40 is a nucleic acid containing oligonucleotide ON1. The reagent components comprise the marker-labeled ligand 44 and nucleic acid-labeled ligand 42; the marker-labeled ligand 44 is a marker-bound nucleic acid with oligonucleotide ON3' having a complementary base sequence to the base sequence of oligonucleotide ON3 in the analyte 43; A nucleic acid-labeled ligand 42 is a nucleic acid, containing oligonucleotide ON2' having a complementary base sequence to the base sequence of oligonucleotide ON2 in the analyte 43 and a bond element oligonucleotide ON1' having a complementary base sequence to the base sequence of the oligonucleotide ON1 in the anti-bond element 41 immobilized on the detection zone 40.

By using the assay kit or assay device containing such reagent in accordance with the present invention, an objective nucleic acid analyte is captured, and its binding model is shown in FIG. 7. While the reagent and a liquid sample are developed in the developing element of the assay device of the present invention, the following reactions occur through the interactive reactions of the analyte, the reagent and the immobilized anti-bond element; the complementary binding between oligonucleotide ON1 in the anti-bond element 41 and oligonucleotide ON1' in the nucleic acid-labeled ligand 42, the complementary binding between oligonucleotide ON2' in the nucleic acid-labeled ligand 42 and oligonucleotide ON2 in the analyte 43, and the complementary binding between oligonucleotide ON3 in the analyte 43 and oligonucleotide ON3' in the marker-labeled ligand 44. Then, a complex containing the maker and analyte 43 is captured on the anti-bond element 41.

According to the assay method of the present invention, complexes of substances with biological affinity, such as immunocomplexes, are generated, prior to loading on the assay device or at an early stage after loading. By the assay device of the present invention, the complementary binding between nucleic acids as bond elements and anti-bond elements to be used for capturing the complexes of substances with biological affinity has a higher degree of agreement at a high stability, which is promoted more strongly than an immune reaction. Hence, such complexes of substances with biological affinity can be bound efficiently to the solid phase. Thus, the assay by means of the assay device is more highly sensitive than by conventional immunochromatography.

When a combination between a nucleic acid and a nucleic acid with a low agreement of complementary binding is selected, in contrast, the detection sensitivity can be controlled by means of the sequence of nucleic acids, without any need to reduce the amount of an antibody with too low sensitivity which eventually occurs when using an antibody at a high titer, because the reaction of a nucleic acid at a low stability is weaker than an immune reaction. Such control can never be realized by conventional immunochromatography. The present invention characteristically can firstly realize the control. When a plurality of items should be determined simultaneously, in particular, individual items have different normal and abnormal ranges, which sometimes demands the modification of the concentration and amount of an antibody. In accordance with the present invention, however, the adjustment can be greatly simplified.

Various methods may be used to immobilize nucleic acids serving as anti-bond elements in the detection zone of the developing element in accordance with the present invention. At 5' or 3' terminus of a nucleic acid as an anti-bond element, or at the position of an appropriate functional group in nucleic acids other than the termini, nucleic acids may satisfactorily be covalently bonded, directly or through an introduced functional group, to a water-insoluble support in the detection zone. Nucleic acids may satisfactorily be bonded covalently, through a nucleic acid actively introduced with a function group or directly or through an introduced functional group, to the water-insoluble support in the detection zone.

As another immobilizing means of nucleic acids in the detection zone, binding may satisfactorily be done by interposing a different substance between them. By preliminarily binding a nucleic acid, for example through bonding due to biological affinity or covalent bonding to a substance immobilizable through physical adsorption on the detection zone, for example, the resulting bound product may then be immobilized through physical adsorption on the detection zone. At the 5' or 3' terminus of a nucleotide or at the position of an appropriate functional group introduced into an appropriate position in the nucleotide, for example, a different substance physically adsorbable onto the detection zone is bonded through the functional group, which is then adsorbed onto the detection zone. For example, protein is a substance physically adsorbable on an insoluble support; for example, SH group is introduced into amino group of the protein, and through the reaction of SH group with maleimide group introduced into 5' terminus of oligonucleotide, the protein is covalently bonded together, which can be immobilized on the detection zone through such physical adsorption.

The binding of a different substance to a nucleic acid may be derived from biological affinity other than the covalent bonding described above. Such different substances include for example, protein. Examples of the protein include avidin, bovine serum albumin, immunoglobulin and the like. When immunoglobulin may have immunological affinity to an analyte, the assay sensitivity can further be enhanced by utilizing the immunological binding with the analyte.

Figure 8:
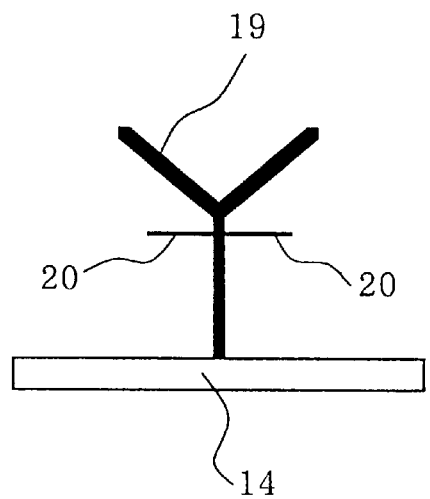
FIG. 8 depicts nucleic acids-labeled IgG antibody containing an anti-bond element consisting of nucleic acids introduced into the IgG antibody on an insoluble support in the detection zone as an assay device for detecting an analyte antigen.

FIG. 8 depicts nucleic acid-labeled IgG antibody 19 with an anti-bond element consisting of nucleic acids 20 introduced into the IgG antibody, at an immobilized state on an insoluble support in the detection zone, as an assay device for detecting an antigen which is the analyte. Two nucleic acids 20, 20 are preliminarily introduced into the nucleic acid-labeled IgG antibody 19 with immunochemical activity, and such nucleic acid-labeled IgG antibody 19 is adsorbed onto the detection zone 14, where the nucleic acid 20 in a state immobilized through the IgG antibody.

Figure 9:
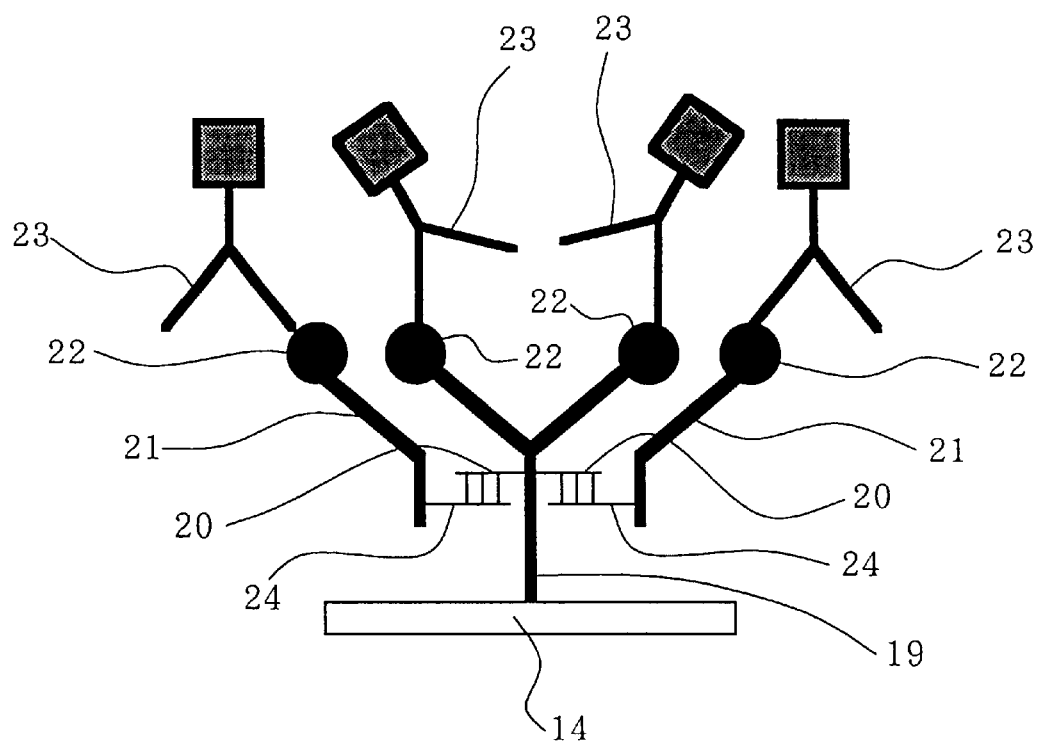
FIG. 9 depicts the state of sandwich immunocomplexes captured on the detection zone shown in FIG. 8.

FIG. 9 depicts the state of a sandwich immunocomplex captured on the detection zone 14 shown in FIG. 8. In FIG. 9, two species of immunocomplexes are captured on the nucleic acid-labeled IgG antibody 19. One of the complexes is a sandwich immunocomplex formed from antigen 22 as the analyte, nucleic acid-labeled antibody 21 and marker-labeled antibody 23. The other complex is an immunocomplex formed from the marker-labeled antibody 23 and antigen 22.

More specifically, by immobilizing the nucleic acid-labeled IgG antibody 19 introduced with nucleic acid 20 into the detection zone 14 in FIG. 9, the antigen 22 is detected due to the complementary binding between the nucleic acid 24 in the nucleic acid-labeled antibody 21 as a reagent component and the nucleic acid 20 in the nucleic acid-labeled IgG antibody 19, but additionally, antigen 22 bound through the immunochemically active action of the IgG antibody of itself is also detected.

According to the conventional method, only two molecules of an assay subject can be bound to one molecule of an immobilized immunochemically active substance; in various embodiments of the present invention, however, more molecules of an antigen as an assay subject can be bound than by the assay of the conventional method, so that more labeling markers can be bound. Therefore, compared to the detection sensitivity of the conventional assay method, the assay method of the present invention has a higher detection sensitivity.

Figure 10:
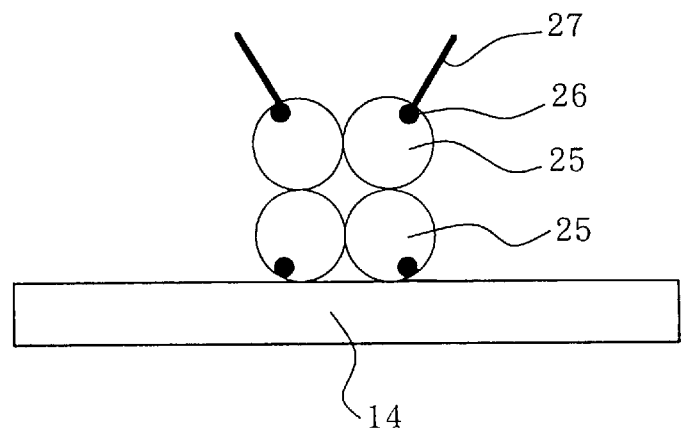
FIG. 10 depicts nucleic acids 27 immobilized through biotin-avidin reaction, by binding biotinylated nucleic acids produced by introducing a biotin into a nucleic acid onto immobilized avidins produced by immobilizing avidins through physical adsorption onto a detection zone.

FIG. 10 depicts nucleic acid 27 immobilized through biotin-avidin reaction, by binding a biotinylated nucleic acid produced by introducing biotin 26 into the nucleic acid 27, onto an immobilized avidin produced by immobilizing avidin through physical adsorption onto detection zone 14.

Figure 11:
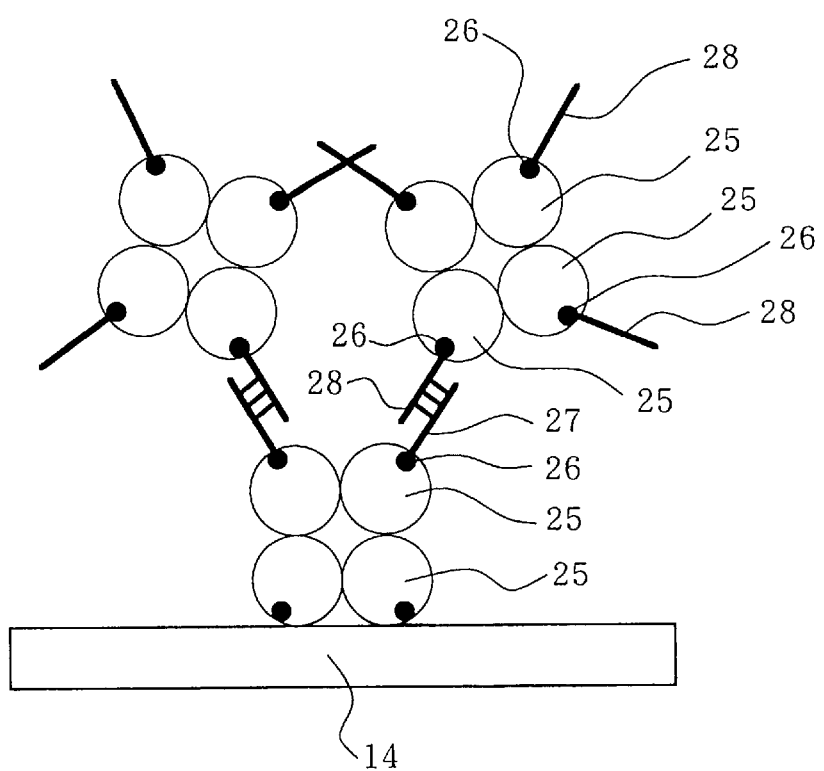
FIG. 11 depicts immobilized nucleic acids as an embodiment different from the nucleic acids immobilized through the biotin-avidin reaction as shown in FIG. 10, wherein nucleic acids-biotin-avidin complex is bound, through complementary binding of nucleic acids, to the nucleic acids-biotins-avidins complex shown in FIG. 10.

FIG. 11 depicts an immobilized nucleic acid as an embodiment different from the nucleic acid immobilized through the biotin-avidin reaction as shown in FIG. 10, wherein a nucleic acid-biotin-avidin complex is bound, through complementary nucleic acid binding to the nucleic acid-biotin-avidin complex shown in FIG. 10, to immobilize the nucleic acid. More specifically, the nucleic acid-biotin-avidin complex prepared, as shown in FIG. 10 is preliminarily bound to the detection zone, and then, a biotinylated nucleic acid produced by introducing biotin 26 into nucleic acid 28 with a complementary base sequence to the sequence of preliminarily immobilized nucleic acid 27 forms a complex together with avidin 25, to which is then bound a complex containing the nucleic acid 28, through the complementary binding with the nucleic acid 27 in the aforementioned nucleic acid-biotin-avidin complex, to immobilize the nucleic acid 28.

The nucleic acid-immobilized detection zone as shown in FIG. 11 is grown three-dimensionally in the detection zone and can therefore contain more nucleic acids as bond elements than the nucleic acid-immobilizing means shown in the embodiment of FIG. 10, so the zone can capture more immunocomplexes, at the resultant high detection sensitivity.

By using streptoavidin in place of avidin used in the previosly described two types of embodiments, a nucleic acid-bound insoluble support can be prepared similarly. In the above manner, the assay device of the present invention can be prepared.

The assay device of the present invention may be used singly at a test strip. Also, the test strip can be placed in a case for use. Because blood, serum and plasma collected from patients are highly likely to be contaminated with infectious microorganisms, the possibility of infection should be taken into account, when the assay device of the present invention is used singly as a test strip. So as to reduce the problematic infection and to directly handle the test strip with hands, the placing and handling of the test strip in a plastic case and the like is a preferable embodiment.

Figure 12:
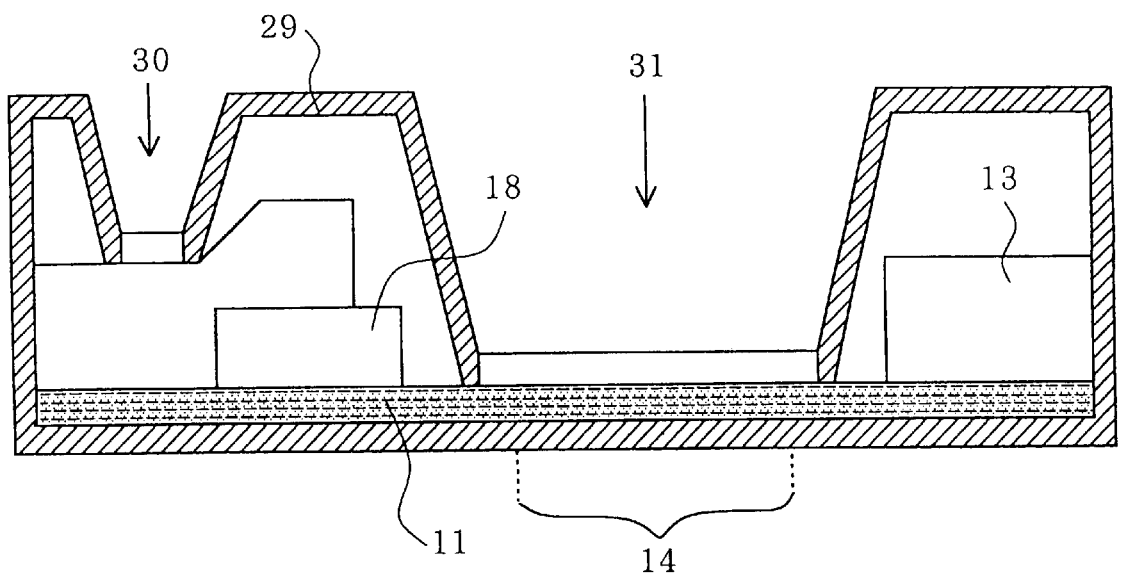
FIG. 12 depicts a means for placing a test strip as the assay device of the present invention into a case.

As a means for placing the test strip in a case, for example, a means shown in FIG. 12 may satisfactorily be used. More specifically, the test strip is preliminarily sealed in a plastic case 29 with two holes, wherein one hole is sample loading hole 30 matched with the loading zone of the test strip while the other hole is detection window 31 in the detection zone where a capturing nucleic acid is bound on the test strip, through which the appearance of the analyte captured can be observed in the detection zone. By means of the test strip placed in the plastic case 29, the possibility of infection through samples by individuals performing microbial laboratory tests can be lowered. Examples of preferable plastics as the material of the plastic case 29 include polyethylene, polystyrene, polypropylene, acrylic resin, ethylene vinyl chloride, polyvinylidene fluoride and the like.

The present invention will now be described in detail in the following examples.

EXAMPLE 1

Process 1: Preparation of Biotinylated Oligonucleotide

As shown below, oligonucleotides each having amino acid at the 5' terminus were individually generated synthetically by using a DNA synthesizer, 391 A, manufactured by Perkin Elmer, Co.

Amino group-GAA TTC CCG GGG ATC CGT CG (referred to as pair 1+ hereinafter) (Seq. I.D. No. 1)

Amino group-CGA CGG ATC CCC GGG AAT TTC (referred to as pair 1− hereinafter) (Seq. I.D. No. 2)

Amino group-AAC CGA ATC TAA TCA GGA GG (referred to as pair 8+ hereinafter) (Seq. I.D. No. 3)

Amino group-CCT CCT GAT TAG ATT CCG TT (referred to as pair 8− hereinafter) (Seq. I.D. No. 4)

These oligonucleotides each of 300 nmol were dissolved in 0.1 M MOPS buffer, pH 7.0 containing 1 mM EDTA, to which was added N-hydroxysuccinimide-biotin (30 µmol; NHS-Biotin manufactured by Pierce, Co.) dissolved in N', N' dimethylformamide (referred to as DMF hereinbelow), for reaction at 37° C. for one hour. After the reaction, biotinylated oligonucleotides were separated by ethanol precipitation. Through the procedure, oligonucleotides each with a sequence biotinylated at almost 80 to 90% were recovered.

Process 2: Preparation of Anti-HBs Antibody and Anti-CRP Antibody

Antibody against Type B hepatitis surface antigen (referred to as HBs hereinbelow) was prepared, by immunizing a rabbit or mouse with HBs purchased from Meiji Milk Products Industry K.K. in a routine manner and preparing a polyclonal antibody from the rabbit or a monoclonal antibody through cloning from the mouse. Antibody against C reactive protein (referred to as CRP hereinbelow) was prepared, by immunizing a rabbit or mouse with CRP purchased from Sapporo Laboratory Test Center in a routine manner and preparing a polyclonal antibody from the rabbit or a monoclonal antibody through cloning from the mouse. The individual antibodies were purified into the state of IgG, which was then subjected to the following experiments.

Process 3: Preparation of Colloidal Gold-labeled Anti-HBs antibody and Colloidal Gold-labeled Anti-CRP Aantibody Rabbit polyclonal anti-HBs antibody prepared in process 2 was labeled with colloidal gold. More specifically, a colloidal gold-labeled rabbit polyclonal anti-HBs antibody was prepared by using colloidal gold of a particle diameter of 10 nm, manufactured by Zaimed, Co. according to the Immunogold method, edited by Yokota et al., Soft Science, 1992. Similarly, the mouse monoclonal anti-CRP antibody was also labeled with colloidal gold.

Process 4: Preparation of Oligonucleotide-labeled Antibody (Anti-CRP-IgG Labeled with pair 8+ (Seq. I.D. No. 3) BSA labeled with Pair 1− (Seq. I.D. No. 2) Anti-HBs-IgG Labeled with Pair 1+) (Seq. I.D. No. 1)

The rabbit polyclonal anti-HBs-IgG (10 mg) recovered at the process 2 was dissolved in 0.2M sodium borate buffer, pH 8.5 (2.3 ml), followed by addition of DMF (0.25 ml) with S-acetylmercaptosuccinic anhydride (1.33 mg) dissolved therein, and the resulting mixture was subjected to reaction at 37° C. for one hour. After the reaction, 1M Tris-HCl buffer, pH 7.0 and 1M hydroxylamine, pH 7.0 were individually added at an amount of 0.5 ml each to the resulting reaction mixture, for further reaction at 37° C. for 30 minutes.

Subsequently, the resulting solution was loaded to a column of a 1-cm diameter and a 45-cm length, preliminarily filled with Sephadex G-25 manufactured by Pharmacia, Co. and equilibrated with 0.1M sodium phosphate buffer, pH 6.0 containing 5 mM EDTA, to recover sulfhydryl group introduced anti-HBs-IgG. Yield of sulfhydryl group introduced anti-HBs-IgG was 9.74 mg. According to the method by Y. Oku et al. (Microbiol. Immunol., 32, 807–816, 1988), the sulfhydryl group was determined. It was confirmed that 2.84 molecules of sulfhydryl group were introduced per one molecule of IgG.

Alternatively, DMF (300 µl) with N-(ε-maleimide-caproyloxy)succinimide (referred to EMCS hereinbelow; 10 mg) dissolved therein was added to 0.1M 3-morpholinopropane sulfonic acid (referred to as MOPS hereinbelow) buffer containing 303 nmol pair 1−, pH 7.0 (0.8 ml), for reaction at 37° C. for 30 minutes. After the reaction, a maleimide group-introduced oligonucleotide was purified by ethanol precipitation. The oligonucleotide was recovered at a yield of 225 nmol. It was confirmed by the determination of the maleimide group that 1.2 molecules of maleimide group was introduced into one molecule of the oligonucleotide.

By subsequently mixing the recovered sulfhydryl group-introduced anti-HBs-IgG with the maleimide group-introduced oligonucleotide and reacting them together at 37° C. for one hour, the resulting mixture was loaded to a column of a 1.5-cm diameter and a 45-cm length, preliminarily equilibrated with 0.1M sodium phosphate buffer, pH 6.0 containing 5 mM EDTA. The absorbance of the resulting fractions was measured at 280 nm and 260 nm, to collect a fraction corresponding to the oligonucleotide-labeled anti-HBs-IgG, which was then concentrated through an ultrafiltration membrane YM-30, manufactured by Millipore, Co.

The protein concentration of the collected fractions was assayed by using a protein assay kit (BCA protein assay kit manufactured by Pierce, Co.). It was indicated that the concentration was 2.12 mg/ml. The complex is now abbreviated as "anti-HBs-IgG labeled with pair 1− " (Seq. I.D. No. 2) hereinbelow.

By the same method as described above, the following labeled products were prepared; anti-CRP-IgG labeled with pair 8+, (Seq. I.D. No. 3) produced by introducing the pair 8+ into the mouse monoclonal anti-CRP-IgG recovered at the process 2; BSA labeled with pair 1−, (Seq. I.D. No. 1) produced by introducing the pair 1− (Seq. I.D. No. 1) into bovine serum albumin (referred to as BSA hereinbelow); and anti-HBs-IgG labeled with pair 1+ (Seq. I.D. No. 1), produced by introducing the pair 1+ into anti-HBs-IgG.

Process 5: Preparation of Oligonucleotide-labeled Anti-HBs-Fab'

The rabbit polyclonal anti-HBs-IgG (12.72 mg) recovered at the process 2 was dissolved in 0.1M sodium acetate buffer, pH 4.5, into which was added pepsin (0.25 mg; Boehringer-Mannheim, Co.) for reaction at 37° C. for 15 hours. After the reaction, the reaction mixture was then loaded to a column of a 1.5-cm diameter and a 45-cm length, preliminarily filled with Ultrogel AcA44 resin manufactured by IBF biotechniqes Co. and equilibrated with 0.1M sodium phosphate buffer, pH 6.0. A fraction corresponding to F(ab')$_2$ was collected and concentrated. Into 4.94 mg of the resulting F(ab')$_2$ was added mercaptoethylamine to a final concentration of 10 mM, for reaction at 37° C. for 90 minutes. After the reaction, the mixture was loaded to a column of a 1.0-cm diameter and a 45-cm length, preliminarily filled with Sephadex G-25 and equilibrated with 0.1M sodium phosphate buffer, pH 6.0. A fraction corresponding to the Fab' with exposed sulfhydryl group at the hinge part was collected and then concentrated with YM-30, to recover sulfhydryl group-introduced Fab'. Fab' (3.3 mg) was recovered. Furthermore, the sulfhydryl group was determined. It was indicated that 1.12 molecules of the sulfhydryl group was introduced per one molecule of Fab'.

Alternatively, the pair 1+ (Seq. I.D. No. 1) oligonucleotide (250 nmol) was dissolved in 0.1M MOPS buffer, pH 7.0 containing 1 mM EDTA, into which was added DMF containing EMCS (7.7 mg), for reaction at 37° C. for one hour. The maleimide group-introduced oligonucleotide was purified through ethanol precipitation and was then dissolved in 0.1M sodium phosphate buffer, pH 6.0 containing 5 mM EDTA. The recovered maleimide group-introduced oligonucleotide was 231 nmol, and it was indicated that 0.73 molecule of maleimide group was introduced per one molecule of the oligonucleotide.

The resulting sulfhydryl group-introduced Fab' and maleimide group-introduced oligonucleotide were mixed together, for reaction at 37° C. for one hour, and after the reaction, the mixture was loaded to a column of a 1.5-cm diameter and a 45-cm length, preliminarily filled with Ultrogel ACA44 and equilibrated with 0.1M sodium phosphate buffer, pH 6.0 containing 5 mM EDTA. The absorbance of the resulting fractions was measured at 280 nm and 260 nm, to collect a fraction corresponding to the oligonucleotide-labeled anti-HBs-Fab', which was then concentrated through an ultrafiltration membrane YM-30, manufactured by Millipore, Co. The protein concentration of the collected fraction was assayed by using a protein assay kit (BCA protein assay kit manufactured by Pierce, Co.). It was indicated that the concentration was 5.72 mg/ml.

Process 6: Preparation of (Pair 1−)-Bound (Seq. I.D. No. 2) Membrane 10 mg of Avidin was dissolved in phosphate buffered physiological saline (20 ml; PBS(−) manufactured by Nissui Pharmaceuticals, Co. Ltd.), and then, a membrane cut into a piece of 5×10 cm (SPHF membrane, manufactured by Millipore, Co.) was immersed in the solution at ambient temperature for one hour and was then rinced with distilled water. After rinsing, the membrane piece was dried in air. By using a soft pen (manufactured by Platinum Fountain Pen Co.) impregnated with 258 nmol/ml biotin-labeled pair 1− (Seq. I.D. No. 2) prepared at the process 1, a line was drawn vertically to the 5-cm side to divide the side in halves, to bind the biotin-labeled pair 1− (Seq. I.D. No. 2) to the avidin-bound SPHF membrane. After drying in air, blocking by means of a blocking agent (Block Ace manufactured by Snow Brand Milk Products, Co.) was effected at ambient temperature for 30 minutes, and subsequently, the resulting membrane was rinsed with distilled water and dried in air, to prepare the (pair 1−)-bound (Seq. I.D. No. 2) membrane. Subsequently, the membrane was cut into a piece of a 0.5-cm width and a 5-cm length, and at one end of the piece was fixed a glass filter (manufactured by Whatman, Co.; referred to as GF hereinbelow) with a staple, and storage under dry conditions.

Process 7: Capture of Sandwich Immunocomplex on Membrane

By using a solution of phosphate buffered physiological saline (manufactured by Nissui Pharmaceuticals Co.; PBS (−)) with addition of 0.1% BSA and 0.35M sodium chloride (referred to as MPBS hereinbelow), (pair 1+)-labeled (Seq. I.D. No. 1) anti-HBs-IgG as prepared at the process 4 was adjusted to a final concentration of 1.54 μg/ml; and colloidal gold prepared at the process 3 (colloidal gold-labeled anti-HBs antibody) was adjusted to an absorbance at 520 nm of 0.5. HBs antigen was then added to the resulting individual labeled products to a final concentration of 100 ng/ml, 50 ng/ml or 0 ng/ml, and 100 μl of each of the solutions was divided to a test tube. The (pair 1−)-bound (Seq. I.D. No. 2) membrane prepared at the process 6 was rapidly placed into the test tube while keeping the GF upward, to examine the reactivity. The reactivity was verified at the HBs final concentrations of 100 ng/ml and 50 ng/ml. No reactivity was confirmed concerning the control solution with no HBs contained therein (0 ng/ml). The results indicate that a sandwich immunocomplex was formed from (pair 1+)-labeled (Seq. I.D. No. 1) anti-HBs-IgG, the HBs antigen and colloidal gold-labeled anti-HBs antibody, wherein the pair 1+ (Seq. I.D. No. 1) in the sandwich immunocomplex and the pair in the (pair 1−)-bound (Seq. I.D. No. 2) membrane were bound together in a complementary manner, whereby the sandwich immunocomplex was captured on the membrane.

EXAMPLE 2

Process 1: Preparation of (Pair 1+)-labeled (Seq. I.D. No. 1) Avidin and (Pair 1−)-labeled (Seq. I.D. No. 2) Avidin The biotin-labeled pair 1+ (Seq. I.D. No. 2) (112 nmol) prepared at the process 1 in Example 1 was reacted with avidin (1.52 mg) in MPBS (0.7 ml) at 37° C. for 3 hours, and subsequently, the mixture was loaded to Ultrogel AcA44 resin manufactured by IBF biotechniqes, preliminarily equilibrated with PBS, to recover pair 1+ labeled avidin. By the same method, additionally, pair 1+ labeled avidin was recovered.

Process 2: Preparation of Oligonucleotide-avidin Matrix-bound Membrane

Avidin (10 mg) was dissolved in phosphate buffered physiological saline (manufactured by Nissui Pharmaceuticals, Co. PBS (−)),and then, membrane cut into a piece of 5×10 cm (SPHF membrane, manufactured by Millipore, Co.) was immersed in the solution at ambient temperature for one hour and was then rinsed with distilled water. After rinsing, the membrane piece was dried in air. By using a soft pen (manufactured by Platinum Fountain Pen Co.) impregnated with 258 nmol/ml biotin-labeled pair 1− (Seq. I.D. No. 1) prepared at the process 1, a line was drawn vertically to the 5-cm side to divide the side in halves, to bind the biotin-labeled pair 1− (Seq. I.D. No. 2) to the avidin-bound SPHF membrane. After drying in air, blocking by means of a blocking agent (Block Ace manufactured by Snow Brand Milk Products, Co.) was effected at ambient temperature for 30 minutes, and subsequently, the resulting membrane was rinsed with distilled water and dried in air, to prepare the (pair 1−)-bound (Seq. I.D. No. 2) SPHF membrane. The (pair 1−)-bound (Seq. I.D. No. 2) SPHF membrane reacted in MPBS containing pair 1+ (Seq. I.D. No. 1) labeled avidin (1 u μ/ml) and pair 1− (Seq. I.D. No. 1) labeled avidin (2 μg/ml),at ambient temperature for one hour, to prepare an oligonucleotide-avidin matrix-bound membrane. The membrane was rinsed with distilled water and dried in air. Subsequently, the membrane was cut into a piece of a 0.5-cm width and a 5-cm length, and at one end of the piece was fixed GF with a staple, and storage under dry conditions.

Process 3: Capture of Sandwich Immunocomplex on Membrane

By using MPBS, (pair 1+)-labeled (Seq. I.D. No. 1) anti-HBs IgG as prepared at the process 4 in Example 1 was adjusted to a final concentration of 1.54 μg/ml and colloidal gold-labeled anti-HBs antibody as prepared at the process 3 in Example 1 was adjusted to an absorbance at 520 nm of 0.5. HBs antigen was then added to the resulting individual labeled products to a final concentration of 100 ng/ml, 80 ng/ml, 60 ng/ml, 40 ng/ml, 20 ng/ml, 0 ng/ml, and 100 μl of each of the solutions was divided to a test tube. The oligonucleotide-avidin matrix-bound membrane prepared at the process 2 in Example 2 was rapidly placed into the test tube while keeping the GF upward, to examine the reactivity. Consequently, the reactivity was verified at the HBs final concentrations of 100 ng/ml, 80 ng/ml, and 60 ng/ml. No reactivity was confirmed at concentrations below 40 ng/ml.

EXAMPLE 3

Process 1: Preparation of (Pair 1−)-bound (Seq. I.D. No. 2) SPHF Membrane

By using a soft pen (manufactured by Platinum Fountain Pen Co.) impregnated with 2 mg/ml (pair 1−)-labeled (Seq. I.D. No. 2) BSA as prepared at the process 4 in Example 1, a line was drawn vertically to the 5-cm side of a membrane cut into a size of 5×10 cm (SPIF membrane; manufactured by Millipore, Co.), to divide the side in halves, to bind the BSA through physical adsorption to the membrane. After drying in air, blocking by means of a blocking agent (Block Ace; manufactured by Snow Brand Milk Products, Co.) was effected at ambient temperature for 30 minutes, and subsequently, the resulting membrane was rinsed with distilled water and dried in air, to prepare (pair 1–)-bound (Seq. I.D. No. 2) SPHF membrane. After drying the membrane in air, the membrane was cut into a piece of a 0.5-cm width and a 5-cm length, and at one end of the piece was fixed GF with a staple, and storage under dry conditions.

Process 2: Capture of Sandwich Immunocomplex on Membrane

By using MPBS, (pair 1+)-labeled (Seq. I.D. No. 1) anti-HBs-IgG as prepared at the process 4 in Example 1 was adjusted to a final concentration of 1.54 µg/ml and colloidal gold-labeled anti-HBs antibody as prepared at the process 3 in Example 1 was adjusted to an absorbance at 520 nm of 0.5. HBs antigen was then added to the resulting individual labeled products to a final concentration of 100 ng/ml, 50 ng/ml, 25 ng/ml, 10 ng/ml, 5 ng/ml or 0 ng/ml, and 100 µl of each of the solutions was divided to a test tube. (Pair 1–)-bound (Seq. I.D. No. 2) SPHF membrane prepared at the process 1 in Example 3 was rapidly placed into the test tube, while keeping the GF upward, to examine the reactivity. Consequently, the reactivity was verified at the HBs final concentrations of 100 ng/ml, 50 ng/ml, 25 ng/ml, 10 ng/ml and 5 ng/ml. No reactivity was confirmed at concentrations at 0 ng/ml.

EXAMPLE 4

Process 1: Preparation of [(Pair 1–) (Seq. I.D. No. 2)+(Anti-HBs-IgG)]-bound SPHF Membrane By using a soft pen (manufactured by Platinum Fountain Pen Co.) impregnated with 0.5 mg/ml (pair 1–)-labeled (Seq. I.D. No. 2) anti-HBs-IgG as prepared at the process 4 in Example 1, a line was drawn vertically to the 5-cm side of a membrane cut into a size of 5×10 cm (SPHF membrane; manufactured by Millipore, Co.), to divide the side in halves, to bind (pair 1–)-labeled (Seq. I.D. No. 2) anti-HBs-IgG through physical adsorption to the membrane. After drying in air, blocking by means of a blocking agent (Block Ace; manufactured by Snow Brand Milk Products, Co.) was effected at ambient temperature for 30 minutes, and subsequently, the resulting membrane was rinsed with distilled water and dried in air, to prepare the [(pair 1–) (Seq. I.D. No. 2)+(anti-HBs-IgG)]-bound SPHF membrane. After drying the membrane in air, the membrane was cut into a piece of a 0.5-cm width and a 5-cm length, and at one end of the piece was fixed GF with a staple, and storage under dry conditions.

Process 2: Capture of Sandwich Immunocomplex on Membrane

By using MPBS, (pair 1+)-labeled (Seq. I.D. No. 1) anti-HBs-Fab' as prepared at the process 5 in Example 1 was adjusted to a final concentration of 1.54 µg/ml and the colloidal gold prepared at the process 3 in Example 1 was adjusted to an absorbance at 520 nm of 0.5. HBs antigen was then added to the resulting individual products to a final concentration of 100 ng/ml, 50 ng/ml, 25 ng/ml, 10 ng/ml, 5 ng/ml, 2.5 ng/ml or 0 ng/ml, and 100 µl (Seq. I.D. No. 2) of each of the solutions was divided to a test tube. The [(pair 1–)+(anti-HBs-IgG)]-bound SPHF membrane prepared in Example 4 was rapidly placed into the test tube, while keeping the GF upward, to examine the reactivity. Consequently, the reactivity was verified at the HBs final concentrations of 100 ng/ml, 50 ng/ml, 25 ng/ml, 10 ng/ml, 5 ng/ml, and 2.5 ng/ml. No reactivity was confirmed at the concentration 0 ng/ml.

EXAMPLE 5

Construction of Assay Device

Figure 13:
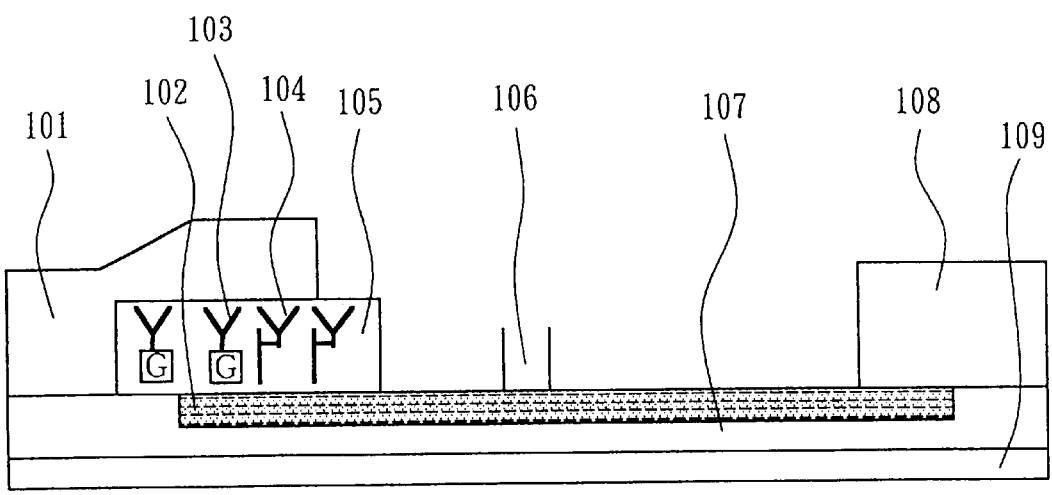
FIG. 13 depicts an assay device in the form of a strip, as used in Example 5.

FIG. 13 depicts an assay device in a strip shape as used in the Example 5. In the strip of FIG. 13, 109 represents overhead projector film manufactured by Highland, Co. for use as the reinforcing support film in the assay device of the Example 5. SPHF membrane strip 102 adheres, through the whole surface of double-sided tape 107 (manufactured by Nichiban, Co.) except both the ends of the double-sided tape 107, to the support film 109, to compose a developing element. The SPHF membrane 102 is prepared at the same process as the process 6 of the Example 1, wherein pair 1– (Seq. I.D. No. 2) is bound at an intermediate position of detection zone 106.

At one end of the developing element is arranged loading zone 101 comprising a filter preliminarily processed with a blocking agent (Block Ace; manufactured by Snow Brand Milk Products, Co.) for blocking, and additionally, sealing zone 105 sealing reagent components is arranged between the loading zone 101 and the developing element and in close contact to the zone and the element, so that a fluid sample loaded might transfer thereon. The sealing zone 105 is made of a glass paper sheet (manufactured by Millipore, Co.) preliminarily processed with a blocking agent (Block Ace; manufactured by Snow Brand Milk Products, Co.) for blocking, and the sealing zone 105 sealing therein colloidal gold-labeled rabbit anti-HBs-IgG 103 (0.15 µg) and (pair 1+)-labeled (Seq. I.D. No. 1) anti-HBs-IgG 104 at a given amount. The colloidal gold-labeled rabbit anti-HBs-IgG 103 is prepared at the process 3 in the Example 1, and the (pair 1+)-labeled anti-HBs-IgG 104 is prepared at the process 4 in the Example 1. On the other end of the developing element is arranged absorption zone 108 comprising GF. The strip for detecting HBs antigen, thus prepared, has a width of 5 mm and a length of 60 mm, and is stored under drying conditions.

Analysis Example

To the loading zone 101 of the assay device for detecting HBs antigen, as constructed at the process of the present Example 5, was added MPBS (100 µl) adjusted to 100 ng/ml HBs antigen, while to the loading zone 101 of another such assay device for detecting HBs antigen was added MPBS (100 µl) never containing any. Thirty minutes later, the reactivity was assessed on the individual assay devices. Coloring of colloidal gold was observed in the detection zone of the strip with addition of 100 ng/ml HBs antigen, but no coloring was observed on the strip with simple addition of MPBS.

EXAMPLE 6

Construction of Assay Device

Nylon membrane (Biodyne C; manufactured by Pall, Co.) was cut into a piece of 5×10 cm, which was then immersed in an EDC solution for 15 minutes and rinsed with distilled water and dried in air, to prepare an activated Biodyne C. On the activated Biodyne C was drawn a line vertically to the 5-cm side to divide the side in halves, by using a soft pen (manufactured by Platinum Fountain Pen, Co.) impregnated with 20 µg/ml amino group introduced the pair 1– (Seq. I.D. No. 2) prepared at the process 1 of the Example 1, to bind the pair 1– (Seq. I.D. No. 2) to the Biodyne C. The Biodyne C was rinsed with distilled water and blocked with a blocking agent (Block Ace; manufactured by Snow Brand Milk Products, Co.), followed by another rinsing and drying in air. After drying in air, the Biodyne C was cut into a piece of a 0.5-cm width and a 5-cm length with a paper cutter, and GF was fixed on one end. Then, the resulting Biodyne C was stored under drying conditions.

For the assay device for detecting HBs antigen, thus constructed, the (pair 1+)-labeled (Seq. I.D. No. 1) anti-HBs-IgG prepared at the process 4 of the Example 1 was adjusted to a final concentration of 1.54 µg/ml and colloidal gold prepared at the process 3 of the Example 1 was adjusted to an absorbance at 520 nm of 0.5, by using MPBS.

Analysis Example

To the loading zone of the assay device for detecting HBs antigen, as constructed at the process of the present Example 6, was added HBs antigen to a final concentration of 20 µg/ml or 0 ng/ml. 100 µl thereof was divided in a test tube. The (pair 1-)-bound (Seq. I.D. No. 2) Biodyne C prepared at the process of the Example 6 was rapidly placed while keeping the GF upward, to examine the reactivity. Consequently, the reactivity was confirmed at the HBs final concentration of 20 µg/ml. No reactivity was confirmed at zero concentration.

EXAMPLE 7

Construction of Assay Device

SPHF membrane cut into a piece of 5×10 cm was immersed in phosphate buffered physiological saline (20 ml; PBS (-); manufactured by Nissui Pharmaceuticals, Co.) dissolving avidin (10 mg) therein, and the membrane was then rinsed with distilled water. On the membrane rinsed and dried in air was drawn a line at a position of 2 cm apart from one end and vertically to the 5-cm side by using a soft pen (manufactured by Platinum Fountain Pen, Co.) impregnated with the biotin-labeled pair 1- at a concentration of 258 nmol/l, as prepared at the process 1 of the Example 1, to bind the biotin-labeled pair 1- to the avidin-bound SPHF membrane. Similarly, a line was vertically drawn at a position of 2 cm apart from the other end by using a soft pen (manufactured by Platinum Fountain Pen, Co.) impregnated with the biotin-labeled pair 8- (Seq. I.D. No. 4), to bind the biotin-labeled pair 8- (Seq. I.D. No. 4) to the avidin-bound SPHF membrane. After drying the (pair 8-)-immobilized (Seq. I.D. No. 4) SPHF membrane generated through biotin-avidin binding in air, the membrane was blocking processed with a blocking agent (Block Ace; manufactured by Snow Brand Milk Products, Co.) at ambient temperature for 30 minutes, and was then rinced with distilled water and subsequently dried in air. After drying in air, the membrane was cut into a piece of a 0.5-cm width and a 5-cm length, and then, GF manufactured by Whatman, Co. was fixed on one end with a staple. The resulting membrane was stored under drying conditions for use as the assay device in Example 7.

Analysis Example

By using MPBS produced by adding 0.1% BSA and 0.35M sodium chloride into phosphate buffered physiological saline (PBS (-); manufactured by Nissui Pharmaceuticals Co.), a test solution was prepared so that the (pair 1+)-labeled (Seq. I.D. No. 1) anti-HBs-IgG and (pair 8+)-labeled (Seq. I.D. No. 3) anti-CRP-IgG, as prepared at the process 4 of the Example 1, might individually be at a final concentration of 1.54 µg/ml; and colloidal gold-labeled anti-HBs-IgG and colloidal gold-labeled anti-CRP-IgG, as prepared at the process 3 of the Example 1, might be at an absorbance at 520 nm of 0.5.

Four different samples were prepared, by adding HBs antigen and CRP antigen both at a final concentration of 100 ng/ml into the test solution, adding only HBs antigen at a final concentration of 100 ng/ml into the solution, adding only CRP antigen at a final concentration of 100 ng/ml, and never adding any of the antigens into the test solution. 100 µl each was divided into individual test tubes. The assay device comprising the (pair 8-)-immobilized (Seq. I.D. No. 4) SPHF membrane prepared at the process of the Example 7 was placed rapidly into the test tubes, while keeping the GF upward, to assess the reactivity. Consequently, the sample containing both the antigens was colored at the binding regions of pair 1- (Seq. I.D. No. 2) and pair 8+ (Seq. I.D. No. 3). The sample containing only the HBs antigen was colored only at the binding region of pair 1- (Seq. I.D. No. 2). The sample containing only the CRP antigen was colored only at the binding region of pair 8+ (Seq. I.D. No. 3). Additionally, the sample never containing any of the antigens was never colored at any of the binding regions of pair 1- (Seq. I.D. No. 2) and pair 8+ (Seq. I.D. No. 2).

EXAMPLE 8

Construction of Assay Device

Figure 14:
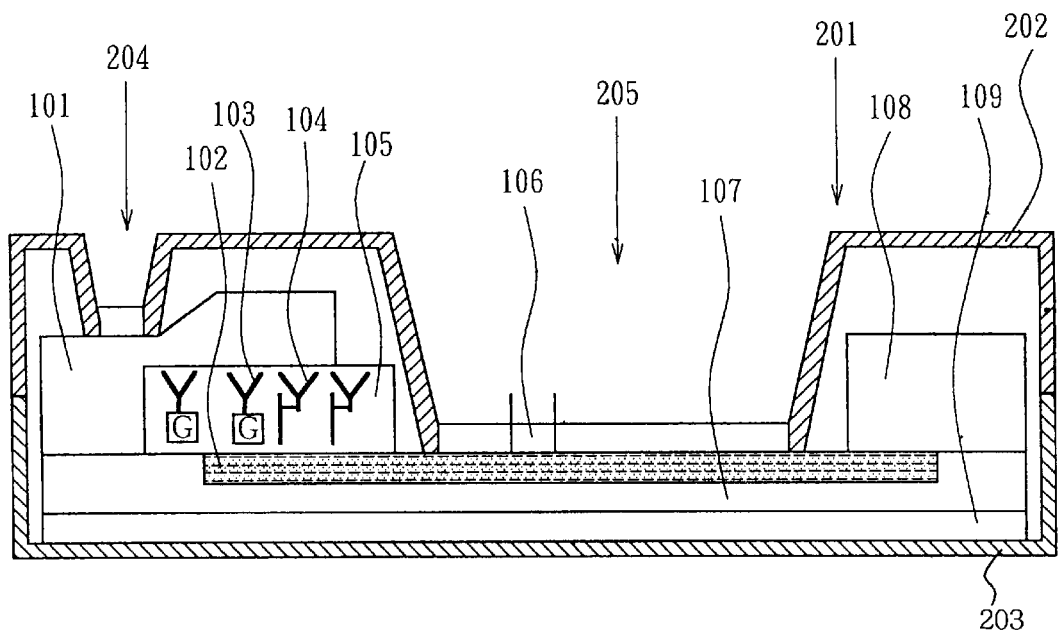
FIG. 14 depicts an assay device used in Example 8, wherein the cross section of the assay device is shown along the length of the strip.
Figure 15:
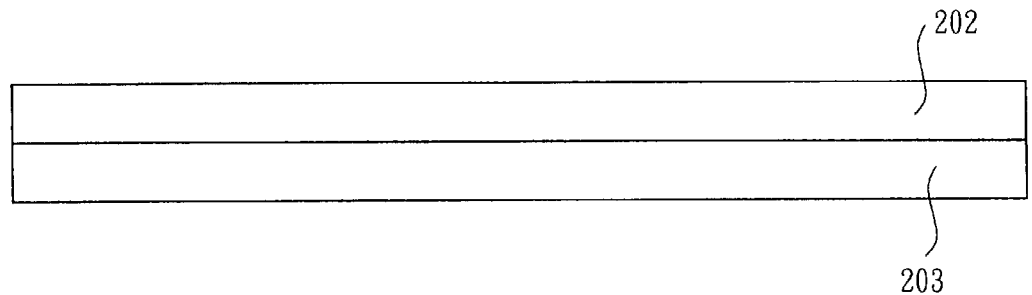
FIG. 15 is a side view of the assay device used in Example 8.
Figure 16:
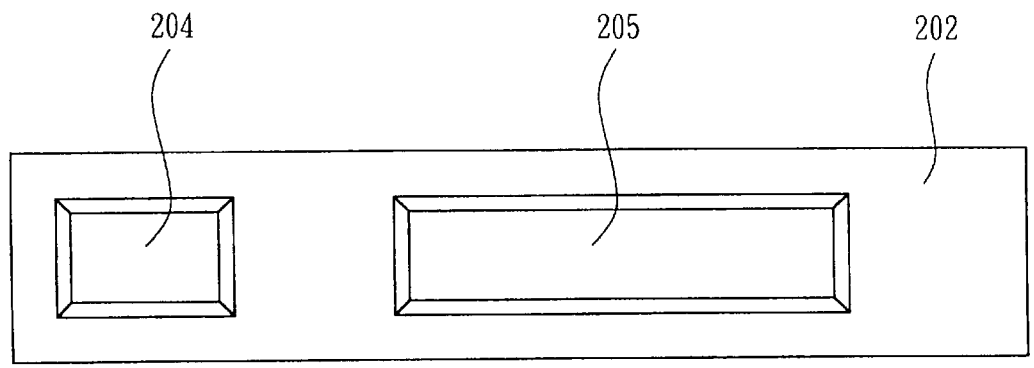
FIG. 16 depicts an assay device used in Example 8, wherein the upper face view of the assay device is shown.

FIGS. 14 to 16 depict the assay device used in the present Example 8; FIG. 14 depicts the cross sectional view along the longitudinal direction of the assay device; FIG. 15 depicts the side view; and FIG. 16 depicts the upper face view. In FIGS. 14 to 16, 201 represents plastic case, composed of upper case 202 and lower case 203. The strip assay device constructed in the Example 5 was arranged in the lower case 203, over which the upper case 202 was placed integrally.

Sample loading opening 204 and detection window 205 are opened at the positions of the upper cases 202, corresponding to the loading zone and detection zone of the strip assay device. By arranging the strip assay device constructed in the Example 5 in the case 201, the HBs antigen detecting assay device of the Example 8 was constructed. The device was stored under drying conditions.

Analysis Example

Through the sample loading opening 204 of the HBs antigen detecting assay device constructed at the process of the Example 8 was added MPBS (100 µl) adjusted to 100 ng/ml HBs antigen, while MPBS (100 µl) never containing any was added into another such HBs antigen detecting assay device prepared additionally, and 30 minutes later, the reactivity in the detection zone 106 bound with pair 1- (Seq. I.D. No. 2) was individually observed through the detection window 205. The coloring of colloidal gold was observed in the assay device with addition of 100 ng/ml HBs antigen, but no coloring thereof was observed in the assay device with addition of only MPBS.

COMPARATIVE EXAMPLE 1

The present Comparative Example 1 is for comparing the detection sensitivity of the conventional method wherein antibodies are immobilized as bond elements on a detection zone, with the detection sensitivity of the present invention.

Construction of Assay Device

By using a soft pen (manufactured by Platinum Fountain Pen to Co.) impregnated with 0.2 mg/ml rabbit anti-HBs-IgG, a line was drawn vertically to the 5-cm side of a membrane cut into a size of 5×10 cm (SPHF membrane; manufactured by Millipore, Co.), to divide the side in halves, to bind the rabbit anti-HBs-IgG through physical adsorption to the SPHF membrane. After drying in air, the membrane was blocked with a blocking agent (Block Ace manufactured by Snow Brand Milk Products, Co.) at ambient temperature for 30 minutes, and subsequently, the resulting membrane was rinsed with distilled water, to recover the rabbit anti-HBs-IgG-bound SPHF membrane. After drying in air, the membrane was cut into a piece of a 0.5-cm width and a 5-cm length, and at one end of the piece was fixed GF with a staple, for storage under dry conditions. The resulting piece was defined as the assay device of the Comparative Example 1. When Go a rabbit anti-HBs-IgG was at a concentration above 0.2 mg/ml, nonspecific reaction was enhanced. Hence, rabbit anti-HBs-IgG at 0.2 mg/ml was used.

Analysis Example

The detection sensitivity of the conventional method was assessed at the following experiments. More specifically, a test solution was prepared so that colloidal gold prepared at the process 3 in the Example 1 might be at absorbance of 0.5 at 520 nm. To the resulting solution was added HBs antigen to a final concentration of 100 ng/ml, 50 ng/ml, 25 ng/ml, 10 ng/ml, 5 ng/ml, 2.5 ng/ml or 0 ng/ml.

100 μl of the resulting each reagent—antigen mixture was divided into a test tube. The assay device of the Comparative Example 1, comprising the anti-HBs-IgG-bound SPHF membrane prepared at the process of the Comparative Example 1, was rapidly placed in the test tubes placing therein the mixture solution of the antigen solution and the reagent, as prepared at the process of the Comparative Example 1, while keeping the GF upward. The reactivity was then assessed. Consequently, the reactivity was confirmed at the final HBs concentrations of 100 ng/ml, 50 ng/ml, 25 ng/ml and 10 ng/ml, but no reactivity was confirmed at a concentration below 10 ng/ml.

The detection sensitivity of the method in accordance with the present invention was alternatively assessed at the following experiments. More specifically, a test solution was prepared by using MPBS, so that the (pair 1+)-labeled (Seq. I.D. No. 1) anti-HBs-Fab' might be at a concentration of 1.54 μg/ml and colloidal gold prepared at the process 3 of the Example 1 might be at absorbance at 520 nm of 0.5. To the resulting solution was added HBs antigen to a final concentration of 100 ng/ml, 50 ng/ml, 25 ng/ml, 10 ng/ml, 5 ng/ml, 2.5 ng/ml or 0 ng/ml.

100 1 of the resulting each reagent-antigen mixture was divided into a test tube. The [(pair 1–)+(anti-HBs-IgG)]-bound (Seq. I.D. No. 2) SPHF membrane prepared in the Example 4, was rapidly placed in the test tubes, while keeping the GF upward. The reactivity was then assessed. Consequently, the reactivity was confirmed at the HBs final concentrations of 100 ng/ml, 50 ng/ml, 25 ng/ml, 10 ng/ml, 5 ng/ml and 2.5 ng/ml.

The results described above indicate that the assay device comprising nucleic acids as the bond element and anti-bond element in accordance with the present invention has a detection sensitivity 4-fold that of the conventional immunochemically active substances as a bond element and an anti-bond element.

INDUSTRIAL APPLICABILITY

In accordance with the present invention, the complementary binding between nucleic acids as an immobilized anti-bond element and nucleic acids as a bond element contained in a generated complex is a highly stable reaction with a high base agreement ratio and can be promoted more strongly than immune reaction, so that biological substance complexes with high affinity can effectively be bound to the solid phase. For immobilization of nucleic acids as the anti-bond elements, through high molecular substances such as protein, nucleic acids of smaller molecules than that of protein can be bound to protein and nucleic acids molecules (anti-bond elements) of a larger number than the number of protein molecules can be bound. Therefore, a larger number of biological substance complexes with high affinity, including analytes, can be captured, which realizes high sensitivity than that of conventional immunochromatography.

In accordance with the present invention, a complex generated through the reaction of an analyte with a marker-labeled first ligand and nucleic acids-labeled ligand is transferred by chromatography and captured in the detection zone to assay the amount thereof or detect the presence thereof, wherein one or more species of analytes to an almost infinite number of analytes can be assayed or detected by forming individual zones corresponding to individual species of analytes because the analytes can be captured through the complementary binding between the immobilized nucleic acids and the nucleic acids contained in the generated complex.

According to the simple clinical laboratory method of the present invention, the detection sensitivity of analytes to be assayed or to be detected can be controlled in a simple manner, by modifying the agreement ratio of the complementary bases between the individual nucleic acids in the complementary binding of the immobilized nucleic acids and the nucleic acids contained in the generated complex. Such feature is specifically advantageous for simultaneous determination of a plurality of items requiring that the normal ranges and abnormal ranges of individual items differ from each other, which essentially requires the modification of the concentrations and amounts of antibodies.

What is claimed is:

1. An assay method for assaying the amounts of different species of analytes present in a fluid sample or detecting the presence or absence thereof, comprising:
   (1) selecting a pair of bond and antibond elements matched for each analyte species, said bond and antibond elements of each pair being nucleic acid sequences having a degree of complementary binding selected in accordance with a level of sensitivity desired of the assay with respect to the matched analyte species, with different degrees of said complementary binding and correspondingly different levels of sensitivity for different analyte species;
   (2) immobilizing each of said anti-bond elements as an independent band on a developing sheet, said independent bands forming a detection zone for said developing sheet;
   (3) loading a fluid sample containing one or more species of analytes on said developing sheet;
   (4) transferring the loaded fluid sample by capillary action through a sealing zone of the developing sheet, said sealing zone containing reagent components including (a) one or more species of marker-labeled ligands each produced by binding a marker to a first ligand specifically reactive to a specific analyte species, and (b) one or more species of bond element-labeled ligands each produced by binding one of the bond elements to a second ligand specifically reactive to the specific analyte species;
   (5) developing one or more species of specific complexes each composed of:
      a) a specific analyte species,
      b) a specific marker-labeled ligand species specifically bound to the specific analyte species, and
      c) a specific bond element-labeled ligand species specifically bound to the specific analyte species;
   (6) capturing each specific complex in a band separately formed in the detection zone, in dependence upon its specific analyte species, through said complementary binding between the bond element and an anti-bond element immobilized on the developing sheet; and
   (7) detecting the marker contained in the band formed in the detection zone as indicative of the presence or absence of said analyte or analytes in the fluid sample or quantifying said marker as indicative of quantity of said analyte or analytes in the fluid sample.

2. The assay method of claim 1 wherein said reagent components are contained in said sealing zone in a dry state.

3. An assay method according to claim 1, wherein the first ligand and second ligand have the same reactivity to said specific analyte species.

4. An assay method according to claim 1, wherein the first ligand and second ligand have different reactivities to said specific analyte species.

5. An assay method according to claim 1, wherein:
   the first ligand and second ligand are composed of nucleic acids;
   the first ligand has a base sequence capable of binding to analyte nucleic acid in a complementary manner; and the second ligand has a base sequence capable of binding to analyte nucleic acid in a complementary manner.

6. An assay method according to claim 1, wherein an anti-bond element is immobilized on the developing element by covalent bonding, through a functional group introduced into the 5' terminus or 3' terminus of the anti-bond element or introduced into a base of the nucleic acid composing the anti-bond element, to a functional group of an insoluble support serving as the developing element.

7. An assay method according to claim 1, wherein an anti-bond element is immobilized on the developing element by bonding thereof, through biotin introduced into the 5' terminus or 3' terminus of the anti-bond element or biotin introduced into a base the nucleic acid composing the anti-bond element, to avidin or streptoavidin preliminarily bound to an insoluble support serving as the developing element.

8. An assay method according to claim 1, wherein an anti-bond element is immobilized on the developing element by covalent bonding thereof, through a functional group introduced into the 5' terminus or 3' terminus of the anti-bond element or introduced into a base of the nucleic acid composing the anti-bond element, to a protein to obtain a nucleic acid-bound protein, being followed by bonding the obtained nucleic acid-bound protein to an insoluble support serving as the developing element.

9. An assay method according to claim 1, wherein the first ligand and second ligand are immunochemically active substances.

10. An assay method according to claim 1, wherein the marker is metal colloid, colored latex or colored liposome.

11. An assay kit for assaying one or more species of analytes in a sample or detecting the presence or absence thereof in a sample, the assay kit comprising a reagent and an assay device separate from the reagent, wherein the reagent includes (a) one or more species of marker-labeled ligands each produced by binding a marker to a first ligand specifically reactive to a specific analyte species, and (b) one or more species of bond element-labeled ligands each produced by binding a bond element of nucleic acids having a base sequence predetermined for the specific analyte species, to a second ligand specifically reactive to the specific analyte species; and wherein the assay device includes a developing element in a sheet form for developing analytes, reagent and analytes bound to the reagent, through capillary action, and plural species of antibond elements, comprising a nucleic acid base sequence complementary to the base sequence of a paired bond element contained in the separate reagent, separately immobilized in separate areas of the detection zone of the developing element, whereby a complex of each analyte species is captured through the complementary binding between the bond element and an anti-bond element in the detection zone, thereby forming an independent band, wherein the base sequences of each pair of said bond and antibond elements are selected to provide a degree of complementary binding in accordance with a level of sensitivity desired of the assay with respect to the analyte species specifically binding the bond element, and wherein different pairs of bond and antibond elements have different degrees of complimentary binding and correspondingly different levels of sensitivity for different analyte species.

12. An assay device for assaying one or more species of analytes present in a sample or detecting the presence or absence thereof in the sample, wherein the assay device includes:

(1) a developing element in a sheet form for developing analytes, reagent and analytes bound to the reagent, through capillary action;

(2) a loading zone for receiving a fluid sample, the loading zone being positioned at one end of the developing element;

(3) a sealing zone containing reagent components sealed therein, said reagent components including one or more species of marker-labeled ligands each produced by binding a marker to a first ligand specifically reactive to a specific analyte species, and one or more species of bond element-labeled ligands each produced by binding a bond element of nucleic acids having a base sequence predetermined for the specific analyte species, to a second ligand specifically reactive to the specific analyte species, the sealing zone being positioned on the developing element close to the loading zone;

(4) a water absorption zone arranged at a position on the developing element apart from the loading zone, for receiving the analytes, reagent and analytes bound to the reagent, from the loading zone by diffusion through the developing element; and (5) a detection zone, positioned on the developing element between the sealing zone and the water absorption zone, wherein plural species of antibond elements, each with a base sequence complementary to one bond element species, are independently immobilized in separate areas of the detection zone, whereby a complex formed from a marker-labeled ligand, an analyte species and a bond element-labeled ligand, is captured and detected in accordance with the analyte species; and, wherein the base sequences of each pair of said bond and antibond elements are selected to provide a degree of complementary binding in accordance with a level of sensitivity desired of the assay with respect to the analyte species specifically binding the bond element, and wherein different pairs of bond and antibond elements have different degrees of complementary binding and correspondingly different levels of sensitivity for different analyte species.

13. An assay device according to claim 12, wherein the first ligand and second ligand are immunochemically active substances.

14. An assay device according to claim 12, wherein the first ligand and second ligand have the same reactivity to the specific analyte species.

15. An assay device according to claim 12, wherein the first ligand and second ligand have different reactivities to the specific analyte species.

16. An assay device according to claim 12, wherein:
the first ligand and second ligand are nucleic acids;
the first ligand has a base sequence capable of binding to an analyte nucleic acid in a complementary manner; and
the second ligand has a base sequence capable of binding to an analyte nucleic acid in a complementary manner.

17. An assay device according to claim 12, wherein an anti-bond element is immobilized on the developing element by covalent bonding, through a functional group introduced into the 5' terminus or 3' terminus of the anti-bond element or introduced into a base of the nucleic acid composing the anti-bond element, to a functional group of an insoluble support serving as the developing element.

18. An assay device according to claim 12, wherein an anti-bond element is immobilized on the developing element by bonding thereof, through biotin introduced into the 5' terminus or 3' terminus of the anti-bond element or biotin introduced into a base of the nucleic acid composing the anti-bond element, to avidin or streptoavidin preliminarily bound to an insoluble support serving as the developing element.

19. An assay device according to claim 12, wherein an anti-bond element is immobilized on the developing element by covalent bonding thereof, through a functional group introduced into the 5' terminus or 3' terminus of the anti-bond element or introduced into a base of the nucleic acid composing the anti-bond element, to a protein to produce a nucleic acid-bound protein, followed by bonding the obtained nucleic acid-bound protein to an insoluble support serving as the developing element.

20. An assay device according to claim 19, wherein the nucleic acid-bound protein is prepared by binding a nucleic acid to bovine serum albumin.

21. An assay device according to claim 19, wherein the nucleic acid-bound protein is prepared by binding a nucleic acid to immunoglobulin.

22. An assay device according to claim 19, wherein the protein has an immunochemical activity to an analyte.

23. An assay device according to claim 12, wherein the marker is selected from metal colloid, colored latex or colored liposome.

24. An assay device according to claim 12, further including a case made of a moisture-proof solid material for housing said assay device.

* * * * *

UNITED STATES PATENT AND TRADEMARK OFFICE
CERTIFICATE OF CORRECTION

PATENT NO. : 6,448,001 B2
DATED : September 10, 2002
INVENTOR(S) : Oku et al.

It is certified that error appears in the above-identified patent and that said Letters Patent is hereby corrected as shown below:

Column 4,
Line 23, "includes," should read -- include: --

Column 5,
Line 61, "at" should read -- in --.

Column 9,
Line 23, "C," should read -- C --.

Column 10,
Line 1, "ON2'" should read -- ON1' --.

Column 11,
Line 64, "prepared," should read -- prepared --.

Column 12,
Line 29, "is a preferable embodiment." should read -- preferred. --

Column 13,
Line 22, "Aantibody" should read -- antibody. --

Column 18,
Line 15, "sealing reagent" should read -- containing sealing reagent --.

Column 21,
Line 46, "100 1" should read -- 100µ1 --.

Column 25,
Line 13, "a base" should read -- a base of --.

Signed and Sealed this

Seventeenth Day of December, 2002

JAMES E. ROGAN
*Director of the United States Patent and Trademark Office*